US008979792B2

(12) United States Patent
Lev et al.

(10) Patent No.: US 8,979,792 B2
(45) Date of Patent: Mar. 17, 2015

(54) INLINE LIQUID DRUG MEDICAL DEVICES WITH LINEAR DISPLACEABLE SLIDING FLOW CONTROL MEMBER

(75) Inventors: Nimrod Lev, Savion (IL); Igor Denenburg, Gadera (IL); Moshe Gilboa, Kfar Saba (IL)

(73) Assignee: Medimop Medical Projects Ltd., Ra'anana (IL)

( * ) Notice: Subject to any disclaimer, the term of this patent is extended or adjusted under 35 U.S.C. 154(b) by 81 days.

(21) Appl. No.: 13/505,881

(22) PCT Filed: Nov. 4, 2010

(86) PCT No.: PCT/IL2010/000915

§ 371 (c)(1), (2), (4) Date: May 3, 2012

(87) PCT Pub. No.: WO2011/058548

PCT Pub. Date: May 19, 2011

(65) Prior Publication Data

US 2012/0323172 A1 Dec. 20, 2012

(30) Foreign Application Priority Data

Nov. 12, 2009 (IL) .......................................... 202070

(51) Int. Cl.
*A61M 37/00* (2006.01)
*A61J 1/20* (2006.01)
(Continued)

(52) U.S. Cl.
CPC .......... *A61J 1/2096* (2013.01); *A61J 2001/201* (2013.01); *A61J 2001/2013* (2013.01); *A61J 2001/2062* (2013.01); *A61J 1/2089* (2013.01); *B65B 3/003* (2013.01)
USPC ............................................ 604/82; 604/411

(58) Field of Classification Search
CPC ......... A61J 1/2096; A61J 1/20; A61J 1/2089; A61J 1/2093; A61J 1/22; A61J 2001/2013; A61M 39/223; A61M 39/22; A61M 2039/224; A61M 2039/1077
USPC .......... 604/87, 82, 85, 90, 91, 411, 412, 414, 604/533, 534
See application file for complete search history.

(56) References Cited

U.S. PATENT DOCUMENTS

| | | | |
|---|---|---|---|
| 62,333 | A | 2/1867 | Holl |
| 1,021,681 | A | 3/1912 | Jennings |

(Continued)

FOREIGN PATENT DOCUMENTS

| | | | |
|---|---|---|---|
| CN | 1950049 | A | 4/2007 |
| DE | 1913926 | A1 | 9/1970 |

(Continued)

OTHER PUBLICATIONS

Grifols Vial Adapter Product Literature, 2 pages, Jan. 2002.

(Continued)

*Primary Examiner* — Quynh-Nhu H Vu
*Assistant Examiner* — Jenna Zhang
(74) *Attorney, Agent, or Firm* — Panitch Schwarze Belisario & Nadel LLP

(57) ABSTRACT

Inline liquid drug medical device having a longitudinal device axis, a housing with a linear displaceable sliding flow control member displaceable along a transverse bore from a first flow control position for establishing flow communication between a first pair of ports for liquid drug reconstitution purposes to a second flow control position for establishing flow communication between a second pair of ports for liquid drug administration purposes, and a manually operated actuating mechanism for applying a linear displacement force for urging the flow control member to slide along the bore from its first flow control position to its second flow control position.

6 Claims, 18 Drawing Sheets

(51) Int. Cl.
*B65B 3/00* (2006.01)
*A61M 5/32* (2006.01)

(56) References Cited

U.S. PATENT DOCUMENTS

| | | | |
|---|---|---|---|
| 1,704,817 A | 3/1929 | Ayers | |
| 1,930,944 A | 10/1933 | Schmitz, Jr. | |
| 2,326,490 A | 8/1943 | Perelson | |
| 2,931,668 A | 4/1960 | Baley | |
| 2,968,497 A | 1/1961 | Treleman | |
| 3,059,643 A | 10/1962 | Barton | |
| D198,499 S | 6/1964 | Harautunelan | |
| 3,484,849 A | 12/1969 | Huebner et al. | |
| 3,618,637 A | 11/1971 | Santomieri | |
| 3,757,981 A | 9/1973 | Harris, Sr. et al. | |
| 3,788,524 A | 1/1974 | Davis et al. | |
| 3,822,700 A | 7/1974 | Pennington | |
| 3,826,261 A | 7/1974 | Killinger | |
| 3,872,992 A | 3/1975 | Larson | |
| 3,885,607 A | 5/1975 | Peltier | |
| 3,938,520 A | 2/1976 | Scislowicz et al. | |
| 3,957,052 A | 5/1976 | Topham | |
| 3,977,555 A | 8/1976 | Larson | |
| 3,993,063 A | 11/1976 | Larrabee | |
| 4,020,839 A | 5/1977 | Klapp | |
| 4,109,670 A | 8/1978 | Slagel | |
| 4,121,585 A | 10/1978 | Becker, Jr. | |
| 4,161,178 A | 7/1979 | Genese | |
| 4,187,848 A | 2/1980 | Taylor | |
| 4,203,067 A | 5/1980 | Fitzky et al. | |
| 4,203,443 A | 5/1980 | Genese | |
| 4,210,173 A | 7/1980 | Choksi et al. | |
| D257,286 S | 10/1980 | Folkman | |
| 4,253,501 A | 3/1981 | Ogle | |
| 4,296,786 A | 10/1981 | Brignola | |
| 4,303,067 A | 12/1981 | Connolly et al. | |
| 4,312,349 A | 1/1982 | Cohen | |
| 4,314,586 A | 2/1982 | Folkman | |
| 4,328,802 A | 5/1982 | Curley et al. | |
| 4,335,717 A | 6/1982 | Bujan et al. | |
| D267,199 S | 12/1982 | Koenig | |
| 4,376,634 A | 3/1983 | Prior et al. | |
| D268,871 S | 5/1983 | Benham et al. | |
| 4,392,850 A | 7/1983 | Elias et al. | |
| 4,410,321 A | 10/1983 | Pearson et al. | |
| 4,411,662 A | 10/1983 | Pearson | |
| D271,421 S | 11/1983 | Fetterman | |
| 4,434,823 A | 3/1984 | Hudspith | |
| 4,465,471 A | 8/1984 | Harris et al. | |
| 4,475,915 A | 10/1984 | Sloane | |
| 4,493,348 A | 1/1985 | Lemmons | |
| 4,505,709 A | 3/1985 | Froning et al. | |
| 4,507,113 A | 3/1985 | Dunlap | |
| D280,018 S | 8/1985 | Scott | |
| 4,532,969 A | 8/1985 | Kwaan | |
| 4,564,054 A | 1/1986 | Gustavsson | |
| 4,573,993 A | 3/1986 | Hoag et al. | |
| 4,576,211 A | 3/1986 | Valentini et al. | |
| 4,581,014 A | 4/1986 | Millerd et al. | |
| 4,588,396 A | 5/1986 | Stroebel et al. | |
| 4,588,403 A | 5/1986 | Weiss et al. | |
| D284,603 S | 7/1986 | Loignon | |
| 4,604,093 A | 8/1986 | Brown et al. | |
| 4,607,671 A | 8/1986 | Aalto et al. | |
| 4,614,437 A | 9/1986 | Buehler | |
| 4,638,975 A | 1/1987 | Iuchi et al. | |
| 4,639,019 A | 1/1987 | Mittleman | |
| 4,667,927 A | 5/1987 | Oscarsson | |
| 4,676,530 A | 6/1987 | Nordgren et al. | |
| 4,683,975 A | 8/1987 | Booth et al. | |
| 4,697,622 A | 10/1987 | Swift et al. | |
| 4,721,133 A | 1/1988 | Sundblom | |
| 4,729,401 A | 3/1988 | Raines | |
| 4,735,608 A | 4/1988 | Sardam | |
| 4,743,229 A | 5/1988 | Chu | |
| 4,743,243 A | 5/1988 | Vaillancourt | |
| 4,752,292 A | 6/1988 | Lopez et al. | |
| 4,758,235 A | 7/1988 | Tu | |
| 4,759,756 A | 7/1988 | Forman et al. | |
| 4,778,447 A | 10/1988 | Velde et al. | |
| 4,787,898 A | 11/1988 | Raines | |
| 4,797,898 A | 1/1989 | Martinez | |
| 4,804,366 A | 2/1989 | Zdeb et al. | |
| 4,832,690 A | 5/1989 | Kuu | |
| 4,834,152 A | 5/1989 | Howson et al. | |
| 4,857,062 A | 8/1989 | Russell | |
| 4,865,592 A | 9/1989 | Rycroft | |
| 4,871,463 A | 10/1989 | Taylor et al. | |
| 4,898,209 A | 2/1990 | Zbed | |
| 4,909,290 A | 3/1990 | Coccia | |
| 4,931,040 A | 6/1990 | Haber et al. | |
| 4,932,944 A | 6/1990 | Jagger et al. | |
| 4,967,797 A | 11/1990 | Manska | |
| D314,050 S | 1/1991 | Sone | |
| D314,622 S | 2/1991 | Andersson et al. | |
| 4,997,430 A | 3/1991 | Van der Heiden et al. | |
| 5,006,114 A | 4/1991 | Rogers et al. | |
| 5,035,686 A | 7/1991 | Crittenden et al. | |
| 5,041,105 A | 8/1991 | D'Alo et al. | |
| 5,045,066 A | 9/1991 | Scheuble et al. | |
| 5,049,129 A | 9/1991 | Zdeb et al. | |
| 5,053,015 A | 10/1991 | Gross | |
| 5,061,248 A | 10/1991 | Sacco | |
| 5,088,996 A | 2/1992 | Kopfer et al. | |
| 5,096,575 A | 3/1992 | Cosack | |
| 5,104,387 A | 4/1992 | Pokorney et al. | |
| 5,113,904 A | 5/1992 | Aslanian | |
| 5,122,124 A | 6/1992 | Novacek et al. | |
| 5,125,908 A | 6/1992 | Cohen | |
| 5,125,915 A | 6/1992 | Berry et al. | |
| D328,788 S | 8/1992 | Sagae et al. | |
| 5,171,230 A | 12/1992 | Eland et al. | |
| 5,201,705 A | 4/1993 | Berglund et al. | |
| 5,201,717 A * | 4/1993 | Wyatt et al. | 604/192 |
| 5,203,771 A | 4/1993 | Melker et al. | |
| 5,203,775 A | 4/1993 | Frank et al. | |
| 5,211,638 A | 5/1993 | Dudar et al. | |
| 5,232,029 A | 8/1993 | Knox et al. | |
| 5,232,109 A | 8/1993 | Tirrell et al. | |
| 5,242,432 A | 9/1993 | DeFrank | |
| 5,247,972 A | 9/1993 | Tetreault | |
| D341,420 S | 11/1993 | Conn | |
| 5,269,768 A | 12/1993 | Cheung | |
| 5,270,219 A | 12/1993 | DeCastro et al. | |
| 5,279,576 A | 1/1994 | Loo et al. | |
| 5,288,290 A | 2/1994 | Brody | |
| 5,300,034 A | 4/1994 | Behnke et al. | |
| 5,301,685 A | 4/1994 | Guirguis | |
| 5,304,163 A | 4/1994 | Bonnici et al. | |
| 5,308,483 A | 5/1994 | Sklar et al. | |
| 5,312,377 A | 5/1994 | Dalton | |
| 5,328,474 A | 7/1994 | Raines | |
| D349,648 S | 8/1994 | Tirrell et al. | |
| 5,334,163 A | 8/1994 | Sinnett | |
| 5,334,179 A | 8/1994 | Poli et al. | |
| 5,342,346 A | 8/1994 | Honda et al. | |
| 5,344,417 A | 9/1994 | Wadsworth, Jr. | |
| 5,350,372 A | 9/1994 | Ikeda et al. | |
| 5,364,386 A | 11/1994 | Fukuoka et al. | |
| 5,364,387 A | 11/1994 | Sweeney | |
| 5,374,264 A | 12/1994 | Wadsworth, Jr. | |
| 5,385,547 A | 1/1995 | Wong et al. | |
| 5,397,303 A | 3/1995 | Sancoff et al. | |
| 5,429,614 A | 7/1995 | Fowles et al. | |
| 5,433,330 A | 7/1995 | Yatsko et al. | |
| 5,445,630 A | 8/1995 | Richmond | |
| 5,445,631 A | 8/1995 | Uchida | |
| 5,451,374 A | 9/1995 | Molina | |
| 5,454,805 A | 10/1995 | Brony | |
| 5,464,111 A | 11/1995 | Vacek et al. | |
| 5,464,123 A | 11/1995 | Scarrow | |
| 5,466,219 A | 11/1995 | Lynn et al. | |
| 5,466,220 A | 11/1995 | Brenneman | |
| 5,470,327 A | 11/1995 | Helgren et al. | |

(56) References Cited

U.S. PATENT DOCUMENTS 5,471,994 A 12/1995 Guirguis
5,472,022 A 12/1995 Michel et al.
5,478,337 A 12/1995 Okamoto et al.
5,492,147 A 2/1996 Challender et al.
D369,406 S 4/1996 Niedospial et al.
5,505,714 A 4/1996 Dassa et al.
5,509,433 A 4/1996 Paradis
5,520,659 A 5/1996 Hedges
5,526,853 A 6/1996 McPhee et al.
5,527,306 A 6/1996 Haining
5,531,695 A 7/1996 Swisher
5,547,471 A 8/1996 Thompson et al.
5,549,577 A 8/1996 Siegel et al.
5,554,128 A 9/1996 Hedges
5,566,729 A 10/1996 Grabenkort et al.
5,569,191 A 10/1996 Meyer
5,573,281 A 11/1996 Keller
5,578,015 A 11/1996 Robb
5,583,052 A 12/1996 Portnoff et al.
5,584,819 A 12/1996 Kopfer
5,591,143 A 1/1997 Trombley, III et al.
5,603,706 A 2/1997 Wyatt et al.
5,607,439 A 3/1997 Yoon
5,611,576 A 3/1997 Guala
5,616,203 A 4/1997 Stevens
5,636,660 A 6/1997 Pfleiderer et al.
5,637,101 A 6/1997 Shillington
5,641,010 A 6/1997 Maier
5,645,538 A 7/1997 Richmond
5,647,845 A 7/1997 Haber et al.
5,651,776 A 7/1997 Appling et al.
5,653,686 A 8/1997 Coulter et al.
5,674,195 A 10/1997 Truthan
5,676,346 A 10/1997 Leinsing
5,685,845 A 11/1997 Grimard
5,699,821 A 12/1997 Paradis
5,702,019 A 12/1997 Grimard
5,718,346 A 2/1998 Weiler
D393,722 S 4/1998 Fangrow, Jr. et al.
5,738,144 A 4/1998 Rogers
5,743,312 A 4/1998 Pfeifer et al.
5,746,733 A 5/1998 Capaccio et al.
5,755,696 A 5/1998 Caizza
5,766,211 A 6/1998 Wood et al.
5,772,630 A 6/1998 Ljungquist
5,772,652 A 6/1998 Zielinski
RE35,841 E 7/1998 Frank et al.
5,776,116 A 7/1998 Lopez et al.
5,782,872 A 7/1998 Muller
5,806,831 A 9/1998 Paradis
5,810,792 A 9/1998 Fangrow, Jr. et al.
D399,559 S 10/1998 Molina
5,817,082 A 10/1998 Niedospial, Jr. et al.
5,820,621 A 10/1998 Yale et al.
5,827,262 A 10/1998 Neftel et al.
5,832,971 A 11/1998 Yale et al.
5,833,213 A 11/1998 Ryan
5,834,744 A 11/1998 Risman
5,839,715 A 11/1998 Leinsing
5,853,406 A 12/1998 Masuda et al.
5,871,110 A 2/1999 Grimard et al.
5,873,872 A 2/1999 Thibault et al.
5,879,337 A 3/1999 Kuracina et al.
5,879,345 A 3/1999 Aneas
5,887,633 A 3/1999 Yale et al.
5,890,610 A 4/1999 Jansen et al.
5,891,129 A 4/1999 Daubert et al.
5,893,397 A 4/1999 Peterson et al.
5,897,526 A 4/1999 Vaillancourt
5,899,468 A 5/1999 Apps et al.
5,902,280 A 5/1999 Powles et al.
5,902,298 A 5/1999 Niedospial, Jr. et al.
D410,740 S 6/1999 Molina
5,911,710 A 6/1999 Barry et al.
5,919,182 A 7/1999 Avallone
5,921,419 A 7/1999 Niedospial, Jr. et al.
5,924,584 A 7/1999 Hellstrom et al.
5,925,029 A 7/1999 Jansen et al.
5,935,112 A 8/1999 Stevens et al.
5,941,848 A 8/1999 Nishimoto et al.
5,944,700 A 8/1999 Nguyen et al.
5,954,104 A 9/1999 Daubert et al.
5,971,181 A 10/1999 Niedospial, Jr. et al.
5,971,965 A 10/1999 Mayer
5,989,237 A 11/1999 Fowles et al.
6,003,566 A 12/1999 Thibault et al.
6,004,278 A 12/1999 Botich et al.
6,019,750 A 2/2000 Fowles et al.
6,022,339 A 2/2000 Fowles et al.
6,036,171 A 3/2000 Weinheimer et al.
6,039,093 A 3/2000 Mrotzek et al.
6,039,302 A 3/2000 Cote, Sr. et al.
D422,357 S 4/2000 Niedospial, Jr. et al.
6,063,068 A 5/2000 Fowles et al.
D427,308 S 6/2000 Zinger
D427,309 S 6/2000 Molina
6,070,623 A 6/2000 Aneas
6,071,270 A 6/2000 Fowles et al.
6,080,132 A 6/2000 Cole et al.
6,086,762 A 7/2000 Guala
6,089,541 A 7/2000 Weinheimer et al.
6,090,091 A 7/2000 Fowles et al.
6,090,093 A 7/2000 Thibault et al.
D430,291 S 8/2000 Jansen et al.
6,099,511 A 8/2000 Devos et al.
6,113,068 A 9/2000 Ryan
6,113,583 A 9/2000 Fowles et al.
6,117,114 A 9/2000 Paradis
6,139,534 A 10/2000 Niedospial, Jr. et al.
6,142,446 A 11/2000 Leinsing
6,146,362 A 11/2000 Turnbull et al.
6,149,623 A 11/2000 Reynolds
6,156,025 A 12/2000 Niedospial, Jr. et al.
6,159,192 A 12/2000 Fowles et al.
6,168,037 B1 1/2001 Grimard
6,171,287 B1 1/2001 Lynn et al.
6,171,293 B1 1/2001 Rowley et al.
6,173,852 B1 1/2001 Browne
6,174,304 B1 1/2001 Weston
6,179,822 B1 1/2001 Niedospial, Jr.
6,179,823 B1 1/2001 Niedospial, Jr.
6,206,861 B1 3/2001 Mayer
6,221,041 B1 4/2001 Russo
6,221,054 B1 4/2001 Martin et al.
6,221,065 B1 4/2001 Davis
6,238,372 B1 5/2001 Zinger et al.
6,245,044 B1 6/2001 Daw et al.
D445,501 S 7/2001 Niedospial, Jr.
D445,895 S 7/2001 Svendsen
6,253,804 B1 7/2001 Safabash
6,258,078 B1 7/2001 Thilly
6,280,430 B1 8/2001 Neftel et al.
6,290,688 B1 9/2001 Lopez et al.
6,296,621 B1 10/2001 Masuda et al.
6,299,131 B1 10/2001 Ryan
6,343,629 B1 2/2002 Wessman et al.
6,348,044 B1 2/2002 Coletti et al.
6,358,236 B1 3/2002 DeFoggi et al.
6,364,866 B1 4/2002 Furr et al.
6,378,576 B2 4/2002 Thibault et al.
6,378,714 B1 4/2002 Jansen et al.
6,379,340 B1 4/2002 Zinger et al.
6,382,442 B1 5/2002 Thibault et al.
6,408,897 B1 6/2002 Laurent et al.
6,409,708 B1 6/2002 Wessman
6,440,107 B1 8/2002 Trombley, III et al.
6,453,949 B1 9/2002 Chau
6,453,956 B2 9/2002 Safabash
6,474,375 B2 11/2002 Spero et al.
6,478,788 B1 11/2002 Aneas
D468,015 S 12/2002 Horppu
6,499,617 B1 12/2002 Niedospial, Jr. et al.
6,503,240 B1 1/2003 Niedospial, Jr. et al.
6,503,244 B2 1/2003 Hayman

(56) References Cited

U.S. PATENT DOCUMENTS 6,520,932 B2 2/2003 Taylor
6,524,278 B1 2/2003 Campbell et al.
6,524,295 B2 2/2003 Daubert et al.
D472,316 S 3/2003 Douglas et al.
6,530,903 B2 3/2003 Wang et al.
6,537,263 B1 3/2003 Aneas
D472,630 S 4/2003 Douglas et al.
6,544,246 B1 4/2003 Niedospial, Jr.
6,551,299 B2 4/2003 Miyoshi et al.
6,558,365 B2 5/2003 Zinger et al.
6,571,837 B2 6/2003 Jansen et al.
6,572,591 B2 6/2003 Mayer
6,575,955 B2 6/2003 Azzolini
6,581,593 B1 6/2003 Rubin et al.
6,582,415 B1 6/2003 Fowles et al.
6,591,876 B2 7/2003 Safabash
6,599,273 B1 7/2003 Lopez
6,601,721 B2 8/2003 Jansen et al.
6,626,309 B1 9/2003 Jansen et al.
6,638,244 B1 10/2003 Reynolds
D482,121 S 11/2003 Harding et al.
D482,447 S 11/2003 Harding et al.
6,651,956 B2 11/2003 Miller
6,652,509 B1 11/2003 Helgren et al.
D483,487 S 12/2003 Harding et al.
D483,869 S 12/2003 Tran et al.
6,656,433 B2 12/2003 Sasso
6,666,852 B2 12/2003 Niedospial, Jr.
6,681,810 B2 1/2004 Weston
6,681,946 B1 1/2004 Jansen et al.
6,682,509 B2 1/2004 Lopez
6,692,478 B1 2/2004 Paradis
6,692,829 B2 2/2004 Stubler et al.
6,695,829 B2 2/2004 Hellstrom et al.
6,699,229 B2 3/2004 Zinger et al.
6,706,022 B1 3/2004 Leinsing et al.
6,706,031 B2 3/2004 Manera
6,715,520 B2 4/2004 Andreasson et al.
6,729,370 B2 5/2004 Norton et al.
6,736,798 B2 5/2004 Ohkubo et al.
6,745,998 B2 6/2004 Doyle
6,746,438 B1 6/2004 Arnissolle
6,752,180 B2 6/2004 Delay
D495,416 S 8/2004 Dimeo et al.
D496,457 S 9/2004 Prais et al.
6,802,490 B2 10/2004 Leinsing et al.
6,832,994 B2 12/2004 Niedospial, Jr. et al.
6,852,103 B2 * 2/2005 Fuller et al. .................. 604/413
6,875,203 B1 4/2005 Fowles et al.
6,875,205 B2 4/2005 Leinsing
6,878,131 B2 4/2005 Novacek et al.
6,890,328 B2 5/2005 Fowles et al.
D506,256 S 6/2005 Miyoshi et al.
6,901,975 B2 6/2005 Aramata et al.
6,945,417 B2 9/2005 Jansen et al.
6,948,522 B2 9/2005 Newbrough et al.
6,949,086 B2 9/2005 Ferguson et al.
6,957,745 B2 10/2005 Thibault et al.
RE38,996 E 2/2006 Crawford et al.
6,994,315 B2 2/2006 Ryan et al.
6,997,916 B2 2/2006 Simas, Jr. et al.
6,997,917 B2 2/2006 Niedospial, Jr. et al.
7,024,968 B2 4/2006 Raudabough et al.
7,070,589 B2 7/2006 Lolachi et al.
7,074,216 B2 7/2006 Fowles et al.
7,083,600 B2 8/2006 Meloul
7,086,431 B2 8/2006 D'Antonio et al.
7,100,890 B2 9/2006 Cote, Sr. et al.
7,140,401 B2 11/2006 Wilcox et al.
7,150,735 B2 12/2006 Hickle
7,192,423 B2 3/2007 Wong
7,195,623 B2 3/2007 Burroughs et al.
7,241,285 B1 7/2007 Dikeman
7,294,122 B2 11/2007 Kubo et al.
7,306,199 B2 12/2007 Leinsing et al.
D561,348 S 2/2008 Zinger et al.
7,326,188 B1 2/2008 Russell et al.
7,326,194 B2 2/2008 Zinger et al.
7,350,764 B2 4/2008 Raybuck
7,354,422 B2 4/2008 Riesenberger et al.
7,354,427 B2 4/2008 Fangrow
7,425,209 B2 9/2008 Fowles et al.
7,435,246 B2 10/2008 Zihlmann
7,452,348 B2 11/2008 Hasegawa
7,470,257 B2 12/2008 Norton et al.
7,470,265 B2 12/2008 Brugger et al.
7,472,932 B2 1/2009 Weber et al.
7,488,297 B2 2/2009 Flaherty
7,491,197 B2 2/2009 Jansen et al.
7,497,848 B2 3/2009 Leinsing et al.
7,523,967 B2 4/2009 Steppe
7,530,546 B2 5/2009 Ryan et al.
D595,420 S 6/2009 Suzuki et al.
D595,421 S 6/2009 Suzuki et al.
7,540,863 B2 6/2009 Haindl
7,540,865 B2 6/2009 Griffin et al.
7,544,191 B2 6/2009 Peluso et al.
D595,862 S 7/2009 Suzuki et al.
D595,863 S 7/2009 Suzuki et al.
7,611,487 B2 11/2009 Woehr et al.
7,611,502 B2 11/2009 Daly
7,615,041 B2 11/2009 Sullivan et al.
7,628,779 B2 12/2009 Aneas
7,632,261 B2 12/2009 Zinger et al.
D608,900 S 1/2010 Giraud et al.
7,654,995 B2 2/2010 Warren et al.
7,670,326 B2 3/2010 Shemesh
7,695,445 B2 4/2010 Yuki
D616,090 S 5/2010 Kawamura
7,713,247 B2 5/2010 Lopez
7,717,886 B2 5/2010 Lopez
7,722,090 B2 5/2010 Burton et al.
D616,984 S 6/2010 Gilboa
7,731,678 B2 6/2010 Tennican et al.
7,743,799 B2 6/2010 Mosler et al.
7,744,581 B2 6/2010 Wallen et al.
7,758,082 B2 7/2010 Weigel et al.
7,762,524 B2 7/2010 Cawthon et al.
7,766,304 B2 8/2010 Phillips
7,771,383 B2 8/2010 Truitt et al.
7,799,009 B2 9/2010 Niedospial, Jr. et al.
7,803,140 B2 9/2010 Fangrow, Jr.
D627,216 S 11/2010 Fulginiti
D630,732 S 1/2011 Lev et al.
7,862,537 B2 1/2011 Zinger et al.
7,867,215 B2 1/2011 Akerlund et al.
7,879,018 B2 2/2011 Zinger et al.
D634,007 S 3/2011 Zinger et al.
7,900,659 B2 3/2011 Whitley et al.
D637,713 S 5/2011 Nord et al.
7,985,216 B2 7/2011 Daily et al.
D644,104 S 8/2011 Maeda et al.
7,993,328 B2 8/2011 Whitley
8,007,461 B2 8/2011 Huo et al.
8,012,132 B2 9/2011 Lum et al.
8,016,809 B2 9/2011 Zinger et al.
8,021,325 B2 9/2011 Zinger et al.
8,025,653 B2 9/2011 Capitaine et al.
8,029,472 B2 10/2011 Leinsing et al.
8,038,123 B2 10/2011 Ruschke et al.
8,066,688 B2 11/2011 Zinger et al.
8,070,739 B2 12/2011 Zinger et al.
8,075,550 B2 12/2011 Nord et al.
8,096,525 B2 1/2012 Ryan
8,105,314 B2 1/2012 Fangrow, Jr.
D655,017 S 2/2012 Mosler et al.
8,122,923 B2 2/2012 Kraus et al.
8,123,736 B2 2/2012 Kraushaar et al.
D655,071 S 3/2012 Davila
8,157,784 B2 4/2012 Rogers
8,167,863 B2 5/2012 Yow
8,172,824 B2 5/2012 Pfeifer et al.
8,177,768 B2 5/2012 Leinsing
8,182,452 B2 5/2012 Mansour et al.

(56) References Cited

U.S. PATENT DOCUMENTS 8,187,248 B2 5/2012 Zihlmann
8,196,614 B2 6/2012 Kriheli
8,197,459 B2 6/2012 Jansen et al.
8,211,069 B2 7/2012 Fangrow, Jr.
8,225,959 B2 7/2012 Lambrecht
8,241,268 B2 8/2012 Whitley
8,262,628 B2 9/2012 Fangrow, Jr.
8,262,641 B2 9/2012 Vedrine et al.
8,267,127 B2 9/2012 Kriheli
D669,980 S 10/2012 Lev et al.
8,287,513 B2 10/2012 Ellstrom et al.
D673,673 S 1/2013 Wang
D674,088 S 1/2013 Lev et al.
D681,230 S 4/2013 Mosler et al.
8,454,573 B2 6/2013 Wyatt et al.
8,469,939 B2 6/2013 Fangrow, Jr.
8,475,404 B2 7/2013 Foshee et al.
8,480,645 B1 7/2013 Choudhury et al.
8,480,646 B2 7/2013 Nord et al.
8,506,548 B2 8/2013 Okiyama
8,511,352 B2 8/2013 Kraus et al.
D690,418 S 9/2013 Rosenquist
8,523,837 B2 9/2013 Wiggins et al.
8,545,476 B2 10/2013 Ariagno et al.
8,551,067 B2 10/2013 Zinger et al.
8,556,879 B2 10/2013 Okiyama
8,562,582 B2 10/2013 Tuckwell et al.
8,608,723 B2 12/2013 Lev et al.
8,628,508 B2 1/2014 Weitzel et al.
8,684,992 B2 4/2014 Sullivan et al.
2001/0000347 A1 4/2001 Hellstrom et al.
2001/0025671 A1 10/2001 Safabash
2001/0029360 A1 10/2001 Miyoshi et al.
2001/0051793 A1 12/2001 Weston
2002/0017328 A1 2/2002 Loo
2002/0066715 A1 6/2002 Niedospial
2002/0087118 A1 7/2002 Reynolds et al.
2002/0087141 A1 7/2002 Zinger et al.
2002/0087144 A1 7/2002 Zinger et al.
2002/0121496 A1 9/2002 Thiebault et al.
2002/0123736 A1 9/2002 Fowles et al.
2002/0127150 A1 9/2002 Sasso
2002/0128628 A1 9/2002 Fathallah
2002/0138045 A1 9/2002 Moen
2002/0173752 A1 11/2002 Polzin
2002/0193777 A1 12/2002 Aneas
2003/0028156 A1 2/2003 Juliar
2003/0036725 A1 2/2003 Lavi et al.
2003/0068354 A1 4/2003 Reif et al.
2003/0073971 A1 4/2003 Saker
2003/0100866 A1 5/2003 Reynolds
2003/0109846 A1 6/2003 Zinger et al.
2003/0120209 A1 6/2003 Jensen et al.
2003/0153895 A1 8/2003 Leinsing
2003/0187420 A1 10/2003 Akerlund et al.
2003/0191445 A1 10/2003 Wallen et al.
2003/0195479 A1 10/2003 Kuracina et al.
2003/0199846 A1 10/2003 Fowles et al.
2003/0199847 A1 10/2003 Akerlund et al.
2004/0024354 A1 2/2004 Reynolds
2004/0039365 A1 2/2004 Aramata et al.
2004/0044327 A1 3/2004 Hasegawa
2004/0073189 A1 4/2004 Wyatt et al.
2004/0153047 A1 8/2004 Blank et al.
2004/0181192 A1 9/2004 Cuppy
2004/0204699 A1 10/2004 Hanly et al.
2004/0217315 A1 11/2004 Doyle
2004/0225274 A1* 11/2004 Jansen et al. .................. 604/411
2004/0236305 A1 11/2004 Jansen et al.
2004/0255952 A1 12/2004 Carlsen et al.
2005/0015070 A1 1/2005 Delnevo et al.
2005/0016626 A1 1/2005 Wilcox et al.
2005/0055008 A1 3/2005 Paradis et al.
2005/0082828 A1 4/2005 Wicks et al.
2005/0124964 A1 6/2005 Niedospial et al.
2005/0137566 A1 6/2005 Fowles et al.
2005/0148994 A1 7/2005 Leinsing
2005/0159724 A1 7/2005 Enerson
2005/0182383 A1 8/2005 Wallen
2005/0209554 A1 9/2005 Landau
2005/0261637 A1 11/2005 Miller
2005/0277896 A1 12/2005 Messerli et al.
2006/0030832 A1 2/2006 Niedospial et al.
2006/0079834 A1 4/2006 Tennican et al.
2006/0089594 A1 4/2006 Landau
2006/0089603 A1 4/2006 Truitt et al.
2006/0095015 A1 5/2006 Hobbs et al.
2006/0106360 A1 5/2006 Wong
2006/0135948 A1 6/2006 Varma
2006/0155257 A1 7/2006 Reynolds
2006/0253084 A1 11/2006 Nordgren
2007/0024995 A1 2/2007 Hayashi
2007/0060904 A1 3/2007 Vedrine et al.
2007/0079894 A1 4/2007 Kraus et al.
2007/0083164 A1 4/2007 Barrelle et al.
2007/0088252 A1 4/2007 Pestotnik et al.
2007/0088293 A1 4/2007 Fangrow
2007/0088313 A1 4/2007 Zinger et al.
2007/0106244 A1 5/2007 Mosler et al.
2007/0112324 A1 5/2007 Hamedi-Sangsari
2007/0156112 A1 7/2007 Walsh
2007/0167904 A1 7/2007 Zinger et al.
2007/0191760 A1 8/2007 Iguchi et al.
2007/0191764 A1 8/2007 Zihlmann
2007/0191767 A1 8/2007 Hennessy et al.
2007/0203451 A1 8/2007 Murakami et al.
2007/0219483 A1 9/2007 Kitani et al.
2007/0244447 A1 10/2007 Capitaine et al.
2007/0244461 A1 10/2007 Fangrow
2007/0244462 A1 10/2007 Fangrow
2007/0244463 A1 10/2007 Warren et al.
2007/0249995 A1 10/2007 Van Manen
2007/0255202 A1 11/2007 Kitani et al.
2007/0265574 A1 11/2007 Tennican et al.
2007/0265581 A1 11/2007 Funamura et al.
2007/0270778 A9 11/2007 Zinger et al.
2007/0287953 A1 12/2007 Ziv et al.
2007/0299404 A1 12/2007 Katoh et al.
2008/0009789 A1* 1/2008 Zinger et al. .................... 604/89
2008/0009822 A1 1/2008 Enerson
2008/0172024 A1 7/2008 Yow
2008/0249479 A1 10/2008 Zinger et al.
2008/0249498 A1 10/2008 Fangrow
2008/0262465 A1 10/2008 Zinger et al.
2008/0287905 A1 11/2008 Hiejima et al.
2008/0294100 A1 11/2008 de Costa et al.
2008/0306439 A1 12/2008 Nelson et al.
2008/0312634 A1 12/2008 Helmerson et al.
2009/0012492 A1 1/2009 Zihlmann
2009/0054834 A1 2/2009 Zinger et al.
2009/0082750 A1 3/2009 Denenburg et al.
2009/0143758 A1 6/2009 Okiyama
2009/0177177 A1 7/2009 Zinger et al.
2009/0177178 A1 7/2009 Pedersen
2009/0187140 A1 7/2009 Racz
2009/0216212 A1 8/2009 Fangrow, Jr.
2009/0267011 A1 10/2009 Hatton et al.
2009/0299325 A1 12/2009 Vedrine et al.
2009/0326506 A1 12/2009 Hasegawa et al.
2010/0010443 A1 1/2010 Morgan et al.
2010/0022985 A1 1/2010 Sullivan et al.
2010/0030181 A1 2/2010 Helle et al.
2010/0036319 A1 2/2010 Drake et al.
2010/0076397 A1 3/2010 Reed et al.
2010/0087786 A1 4/2010 Zinger et al.
2010/0137827 A1 6/2010 Warren et al.
2010/0160889 A1 6/2010 Smith et al.
2010/0168712 A1 7/2010 Tuckwell et al.
2010/0179506 A1 7/2010 Shemesh et al.
2010/0204670 A1 8/2010 Kraushaar et al.
2010/0228220 A1 9/2010 Zinger et al.
2010/0241088 A1 9/2010 Ranalletta et al.
2010/0274184 A1 10/2010 Chun
2010/0286661 A1 11/2010 Raday et al.

(56) References Cited

U.S. PATENT DOCUMENTS

| | | | |
|---|---|---|---|
| 2010/0312220 | A1 | 12/2010 | Kalitzki |
| 2011/0004184 | A1 | 1/2011 | Proksch et al. |
| 2011/0054440 | A1 | 3/2011 | Lewis |
| 2011/0087164 | A1 | 4/2011 | Mosler et al. |
| 2011/0160701 | A1 | 6/2011 | Wyatt et al. |
| 2011/0175347 | A1 | 7/2011 | Okiyama |
| 2011/0218511 | A1 | 9/2011 | Yokoyama |
| 2011/0224640 | A1 | 9/2011 | Kuhn et al. |
| 2011/0230856 | A1 | 9/2011 | Kyle et al. |
| 2011/0264037 | A1 | 10/2011 | Foshee et al. |
| 2011/0264069 | A1 | 10/2011 | Bochenko |
| 2011/0276007 | A1 | 11/2011 | Denenburg |
| 2011/0319827 | A1 | 12/2011 | Leinsing et al. |
| 2012/0022469 | A1 | 1/2012 | Alpert |
| 2012/0053555 | A1 | 3/2012 | Ariagno et al. |
| 2012/0059346 | A1 | 3/2012 | Sheppard et al. |
| 2012/0067429 | A1 | 3/2012 | Mosler et al. |
| 2012/0078214 | A1 | 3/2012 | Finke et al. |
| 2012/0123382 | A1 | 5/2012 | Kubo |
| 2012/0215182 | A1 | 8/2012 | Mansour et al. |
| 2012/0220977 | A1 | 8/2012 | Yow |
| 2012/0265163 | A1 | 10/2012 | Cheng et al. |
| 2012/0271229 | A1 | 10/2012 | Lev et al. |
| 2012/0296307 | A1 | 11/2012 | Holt et al. |
| 2012/0310203 | A1 | 12/2012 | Khaled et al. |
| 2012/0323187 | A1 | 12/2012 | Iwase et al. |
| 2012/0323210 | A1 | 12/2012 | Lev et al. |
| 2013/0053814 | A1 | 2/2013 | Mueller-Beckhaus et al. |
| 2013/0096493 | A1 | 4/2013 | Kubo et al. |
| 2013/0199669 | A1 | 8/2013 | Moy et al. |
| 2013/0231630 | A1 | 9/2013 | Kraus et al. |
| 2013/0237904 | A1 | 9/2013 | Deneburg et al. |
| 2013/0289530 | A1 | 10/2013 | Wyatt et al. |
| 2014/0096862 | A1 | 4/2014 | Aneas |
| 2014/0150911 | A1 | 6/2014 | Hanner et al. |

FOREIGN PATENT DOCUMENTS

| | | | | |
|---|---|---|---|---|
| DE | 4122476 | A1 | | 1/1993 |
| DE | 19504413 | A1 | | 8/1996 |
| DE | 202004012714 | U1 | | 11/2004 |
| DE | 202009011019 | U1 | | 12/2010 |
| EP | 0192661 | A1 | | 9/1986 |
| EP | 0195018 | A1 | | 9/1986 |
| EP | 0258913 | A2 | | 3/1988 |
| EP | 0416454 | A2 | | 3/1991 |
| EP | 0518397 | A1 | | 12/1992 |
| EP | 0521460 | A1 | | 1/1993 |
| EP | 0637443 | A1 | | 2/1995 |
| EP | 0737467 | A1 | | 10/1996 |
| EP | 761562 | A1 | | 3/1997 |
| EP | 765652 | A1 | | 4/1997 |
| EP | 765853 | A1 | | 4/1997 |
| EP | 0806597 | A1 | | 11/1997 |
| EP | 0814866 | A1 | | 1/1998 |
| EP | 0856331 | A2 | | 8/1998 |
| EP | 829248 | A2 | | 9/1998 |
| EP | 882441 | A2 | | 12/1998 |
| EP | 0887085 | A2 | | 12/1998 |
| EP | 0887885 | A2 | | 12/1998 |
| EP | 897708 | A2 | | 2/1999 |
| EP | 089851 | A2 | | 3/1999 |
| EP | 960616 | A2 | | 12/1999 |
| EP | 1008337 | A1 | | 6/2000 |
| EP | 1029526 | A1 | | 8/2000 |
| EP | 1034809 | A1 | | 9/2000 |
| EP | 1051988 | A2 | | 11/2000 |
| EP | 1323403 | A1 | | 7/2003 |
| EP | 1329210 | A1 | | 7/2003 |
| EP | 1396250 | A1 | | 3/2004 |
| EP | 1454609 | A1 | | 9/2004 |
| EP | 1454650 | A1 | | 9/2004 |
| EP | 1498097 | A2 | | 1/2005 |
| EP | 1872824 | A1 | | 1/2008 |
| EP | 1911432 | A1 | | 4/2008 |
| EP | 1919432 | A1 | | 5/2008 |
| EP | 1930038 | A2 | | 6/2008 |
| EP | 2090278 | A1 | | 8/2009 |
| EP | 2351548 | A1 | | 8/2011 |
| EP | 2351549 | A1 | | 8/2011 |
| EP | 2462913 | A1 | | 6/2012 |
| FR | 2029242 | A5 | | 10/1970 |
| FR | 2856660 | A1 | | 12/2004 |
| FR | 2869795 | A1 | | 11/2005 |
| FR | 2931363 | A1 | | 11/2009 |
| GB | 1444210 | A | | 7/1976 |
| IL | 171662 | | | 10/2005 |
| JP | 03-062426 | B | | 9/1991 |
| JP | 4329954 | A | | 11/1992 |
| JP | 06-050656 | U | | 7/1994 |
| JP | H08-000170 | A | | 1/1996 |
| JP | 09-104460 | A | | 4/1997 |
| JP | 09-104461 | A | | 4/1997 |
| JP | 10-118158 | A | | 5/1998 |
| JP | H10-504736 | A | | 5/1998 |
| JP | 11503627 | T | | 3/1999 |
| JP | 11-319031 | A | | 11/1999 |
| JP | 2000-508934 | A | | 7/2000 |
| JP | 2000-237278 | A | | 9/2000 |
| JP | 2001-505083 | A | | 4/2001 |
| JP | 2002-035140 | A | | 2/2002 |
| JP | 2002-516160 | A | | 6/2002 |
| JP | 2002-355318 | A | | 12/2002 |
| JP | 2003-033441 | A | | 2/2003 |
| JP | 2003-102807 | A | | 4/2003 |
| JP | 2004-097253 | A | | 4/2004 |
| JP | 2004-522541 | A | | 7/2004 |
| JP | 2010-179128 | A | | 8/2010 |
| WO | 9003536 | A1 | | 4/1990 |
| WO | 9403373 | A1 | | 2/1994 |
| WO | 9507066 | A1 | | 3/1995 |
| WO | 9600053 | A1 | | 1/1996 |
| WO | 9629113 | A1 | | 9/1996 |
| WO | 9736636 | A1 | | 10/1997 |
| WO | 9832411 | A1 | | 7/1998 |
| WO | 9837854 | A1 | | 9/1998 |
| WO | 9961093 | A1 | | 12/1999 |
| WO | 0128490 | A1 | | 4/2001 |
| WO | 0130425 | A1 | | 5/2001 |
| WO | 0132524 | A1 | | 5/2001 |
| WO | 0160311 | A1 | | 8/2001 |
| WO | 0191693 | A2 | | 12/2001 |
| WO | 0209797 | A1 | | 2/2002 |
| WO | 0232372 | A1 | | 4/2002 |
| WO | 0236191 | A2 | | 5/2002 |
| WO | 02066100 | A2 | | 8/2002 |
| WO | 02089900 | A1 | | 11/2002 |
| WO | 03051423 | A2 | | 6/2003 |
| WO | 03070147 | A2 | | 8/2003 |
| WO | 03079956 | A1 | | 10/2003 |
| WO | 2004041148 | A1 | | 5/2004 |
| WO | 2005002492 | A1 | | 1/2005 |
| WO | 2005041846 | A2 | | 5/2005 |
| WO | 2005105014 | A2 | | 11/2005 |
| WO | WO 2005105014 | A2 | * | 11/2005 |
| WO | WO 2006085327 | A1 | * | 8/2006 |
| WO | 2006099441 | A2 | | 9/2006 |
| WO | 2007015233 | A1 | | 2/2007 |
| WO | 2007017868 | A1 | | 2/2007 |
| WO | 2007052252 | A1 | | 5/2007 |
| WO | 2007101772 | A1 | | 9/2007 |
| WO | 2007105221 | A1 | | 9/2007 |
| WO | 2008081424 | A2 | | 7/2008 |
| WO | WO 2008126090 | A1 | * | 10/2008 |
| WO | 2009026443 | A2 | | 2/2009 |
| WO | 2009029010 | A1 | | 3/2009 |
| WO | 2009038860 | A1 | | 3/2009 |
| WO | 2009038860 | A2 | | 3/2009 |
| WO | 2009040804 | A2 | | 4/2009 |
| WO | 2009087572 | A1 | | 7/2009 |
| WO | 2009093249 | A1 | | 7/2009 |
| WO | 2009112489 | A1 | | 9/2009 |
| WO | 2009146088 | A1 | | 12/2009 |

(56) References Cited

FOREIGN PATENT DOCUMENTS

| | | | |
|---|---|---|---|
| WO | 2010061743 | A1 | 6/2010 |
| WO | 2010117580 | A1 | 10/2010 |
| WO | 2011039747 | A1 | 4/2011 |
| WO | 2011058545 | A1 | 5/2011 |
| WO | 2011058548 | A1 | 5/2011 |
| WO | 2011077434 | A1 | 6/2011 |
| WO | 2011104711 | A1 | 9/2011 |
| WO | 2012063230 | A1 | 5/2012 |
| WO | 2012143921 | A1 | 10/2012 |
| WO | 2013127813 | A1 | 9/2013 |
| WO | 2013134246 | A1 | 9/2013 |
| WO | 2013156944 | A1 | 10/2013 |
| WO | 2014033710 | A1 | 3/2014 |

OTHER PUBLICATIONS

Novel Transfer, Mixing and Drug Delivery Systems, MOP Medimop Medical Projects Ltd. Catalog, 4 pages, Rev. 4, 2004.
Smart Site.RTM. Alaris Medical Systems Product Brochure, 4 pages, Issue 1, Oct. 1999.
Smart Site.RTM. Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM Valve, B. Braun Medical, Inc. website and product description, 3 pages, Feb. 2006.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/en/products/pp./Mixject.aspx.
http://www.westpharma.com/eu/SiteCollectionDocuments/Recon/mixject%20product%20sheet.pfg: MIXJECT product information sheet pp. 1.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376.
Int'l Search Report Issued Aug. 25, 2008 in Int'l Application No. PCT/IL2008/000517.
Written Opinion of the ISR Issued in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued Feb. 3, 2011 in Int'l Application No. PCT/IL2010/000777.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
Int'l Search Report issued Oct. 7, 2011 in Int'l Application No. PCT/IL2011/000511.
Int'l Search Report issued Mar. 6, 2012 in Int'l Application No. PCT/IL2011/000834; Written Opinion.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 2008801108283.4.
Office Action issued Mar. 6, 2012 in U.S. Appl. No. 12/678,928.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
Int'l Search Report & Written Opinion issued on Mar. 7, 2012 in Int'l Application No. PCT/IL2011/000829.
Office Action issued May 31, 2013 in U.S. Appl. No. 13/505,790.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
Int'l Search Report issued Jan. 22, 2013 in Int'l Application No. PCT/IL2012/000354.
Int'l Search Report issued Mar. 18, 2013 in Int'l Application No. PCT/IL2012/050516.
Office Action issued Apr. 2, 2013 in U.S. Appl. No. 13/505,790.
Int'l Search Report and Written Opinion issued Mar. 6, 2012 in Int'l Application No. PCT/IL2011/000834.
Int'l Search Report issued Aug. 16, 2012 in Int'l Application No. PCT/IL2012/000164.
Written Opinion issued Aug. 16, 2012 in Int'l Application No. PCT/IL2012/000164.
English translation of an Office Action issued Sep. 10, 2013 in JP Application No. 2012-554468.
Int'l Search Report and Written Opinion issued Jan. 7, 2014 in Int'l Application No. PCT/IL2013/050721.
English translation of an Office Action issued Jan. 9, 2014 in JP Application No. 2010-526421.

(56) References Cited

OTHER PUBLICATIONS

English translation of an Office Action issued Dec. 4, 2013 in CN Application No. 201080051210.3.
English translation of an Office Action issued Dec. 25, 2013 in CN Application No. 201180006530.1.
Office Action issued Nov. 28, 2013 in IN Application No. 4348/DELNP/2008.
Office Action issued Oct. 8, 2013 in CN Application No. 201080043825.1.
International Search Report Issued Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Drug Adminsitration Systems product information sheets; http://www.westpharma.com/eu/en/products/Pages/Vial2Bag.aspx; pp. 1-3 (admitted prior art).
Office Action Issued Jun. 8, 2010 in U.S. Appl. No. 12/112,490 by Zinger.
Office Action issued Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
Office Action issued Jun. 15, 2011 in JP Application No. 2008-538492.
Translation of Office Action issued Jun. 18, 2012 in JP Application No. 2008-538492.
Translation of Office Action issued Apr. 15, 2013 in JP Application No. 2008-538492.
Office Action issued Jul. 13, 2012 in U.S. Appl. No. 12/112,490 by Zinger.
Office Action issued Jan. 23, 2013 in U.S. Appl. No. 12/112,490 by Zinger.
Int'l Preliminary Report on Patentability issued May 6, 2008 in Int'l Application No. PCT/IL2006/001228.
Int'l Preliminary Report on Patentability issued Sep. 24, 2013 in Int'l Application No. PCT/IL2012/000354.
Office Action issued Feb. 13, 2014 in U.S. Appl. No. 13/884,981 by Denenburg.
U.S. Appl. No. 14/345,094 by LEV, filed Mar. 14, 2014.
Int'l Search Report issued Jun. 19, 2013 in Int'l Application No. PCT/IL2013/050167.
Int'l Preliminary Report on Patentability issued Aug. 28, 2012 in Int'l Application No. PCT/IL2011/000186.
U.S. Appl. No. 14/005,751 by Denenburg, filed Sep. 17, 2013.
English translation of an Office Action issued Jul. 26, 2013 in JP Application No. 2012-538464.
Int'l Search Report issued Jun. 5, 2013 in Int'l Application No. PCT/IL2012/050407.
Int'l Search Report issued Jun. 19, 2013 in Int'l Application No. PCT/IL201/050167.
Int'l Search Report issued Jul. 1, 2013 in Int'l Application No. PCT/IL2013/050180.
Int'l Search Report issued Jul. 31, 2103 in Int'l Application No. PCT/IL2013/050313.
Int'l Search Report issued Jul. 26, 2013 in Int'l Application No. PCT/IL2013/050316.
English translation of an Office Action issued Jun. 19, 2013 in JP Application No. 2012-531551.
Office Action issued Aug. 20, 2013 in U.S. Appl. No. 13/576,461 by LEV.
Office Action issued Nov. 11, 2013 in IL Application No. 218730.
U.S. Appl. No. 29/478,723 by LEV, filed Jan. 8, 2014.
U.S. Appl. No. 29/478,726 by LEV, filed Jan. 8, 2014.
U.S. Appl. No. 14/366,306 by LEV, filed Jun. 18, 2014.
Office Action issued Apr. 17, 2014 in CN Application No. 201080051201.4.
Int'l Search Report and Written Opinion issued May 8, 2014 in Int'l Application No. PCT/IL2013/050706.
English translation of an Office Action issued Apr. 28, 2014 in JP Application No. 2013-537257.
Int'l Search Report and Written Opinion issued Jul. 16, 2014 in Int'l Application No. PCT/IL2014/050327.
English translation of an Office Action issued Jun. 30, 2014 in CN Application No. 201180052962.6.
Extended European Search Report issued Jun. 3, 2014 in EP Application No. 08781828.2.
Office Action issued Jul. 31, 2014 in U.S. Appl. No. 29/438,141, by Gilboa.
U.S. Appl. No. 14/385,212 by Lev, filed Sep. 15, 2014.
U.S. Appl. No. 29/502,037 by Lev, filed Sep. 11, 2014.
U.S. Appl. No. 29/502,053 by Lev, filed Sep. 11, 2014.
U.S. Appl. No. 14/391,792 by Lev, filed Oct. 10, 2014.
U.S. Appl. No. 14/504,979 by Lev, filed Oct. 2, 2014.
Int'l Search Report and Written Opinion issued Sep. 2, 2014 in Int'l Application No. PCT/IL2014/050405.
Int'l Search Report and Written Opinion issued Oct. 17, 2014 in Int'l Application No. PCT/IL2014/050680.
English translation of an Office Action issued Aug. 28, 2014 in JP Application No. 2013-168885.

* cited by examiner

S1>S2

INLINE LIQUID DRUG MEDICAL DEVICES WITH LINEAR DISPLACEABLE SLIDING FLOW CONTROL MEMBER

CROSS-REFERENCE TO RELATED APPLICATION

This application is a Section 371 of International Application No. PCT/IL2010/000915, filed Nov. 4, 2010, which was published in the English language on May 19, 2011, under International Publication No. WO 2011/058548 A1, and the disclosure of which is incorporated herein by reference.

FIELD OF THE INVENTION

The invention relates to inline liquid drug medical devices for liquid drug reconstitution and administration purposes.

BACKGROUND OF THE INVENTION

Commonly owned U.S. Pat. No. 6,238,372 entitled Fluid Control Device illustrates and describes a fluid control device for use with a syringe and at least one medicinal vessel. The fluid control device includes a first port, a second port for receiving the syringe, a third port including an adaptor having a fluid conduit member extending into the interior of the medicinal vessel when attached thereto and a flow control member selectively disposable from a first flow control position enabling a flow path between a first pair of two ports and second flow control position enabling a flow path between a second pair of two ports. The flow control member is coupled to one of the ports for manipulation between its flow control positions.

Commonly owned PCT International Application No. PCT/IL2005/000376 entitled Liquid Drug Medical Devices and published under PCT International Publication No. WO 2005/105014 illustrates and describes a liquid drug medical device for liquid drug reconstitution and administration purposes, a vial adapter with elastomer tubing and a needle shield removal device. The liquid drug medical device has a longitudinal axis and is intended for use with a source of physiological solution and a medicinal vessel. The liquid drug medical device includes a body member having a first port for fluid connection with the source of physiological solution and a flow control member rotatably mounted in the body member about an axis of rotation co-directional with the longitudinal axis. The flow control member has a first major flow duct and a second major flow duct substantially parallel to and non-coaxial with the axis of rotation and respectively terminating at a second port, and a third port for administering the liquid drug. The liquid drug medical device further includes a manually rotatable adapter having a fluid conduit member with a proximal end in flow communication with the second port and a distal end extending into the medicinal vessel on its attachment to the adapter, and coupled to the flow control member for rotating same between a first flow control position for connecting the first port with the second port, and a second flow control position for connecting the first port with the third port.

Commonly owned PCT International Application No. PCT/US2008/070024 entitled Medicament Mixing and Injection Apparatus and published under PCT International Publication No. WO 2009/038860 illustrates and describes a mixing and injection apparatus including a needle and a needle base, a syringe attachment element and a mixing chamber engagement assembly including a needle chamber surrounding the needle and a first liquid conduit portion, sealed from the needle chamber and a mixing chamber engagement portion including a second liquid conduit portion communicating with the first liquid conduit portion and configured for communication with a mixing chamber. The syringe attachment element and the needle base are configured to permit liquid communication between an interior of the syringe and the first liquid conduit portion when the syringe attachment element and the needle base are in the first relative engagement orientation and to permit liquid communication between an interior of the syringe and the needle when the syringe attachment element and the needle base are in the second relative engagement orientation, axially separated from the first relative orientation along the injection axis.

SUMMARY OF THE INVENTION

The present invention is directed toward inline liquid drug medical devices for use with a source of physiological fluid and a medicinal vessel for liquid drug reconstitution and administration purposes.

The inline liquid drug medical device includes a housing having a longitudinal device axis and a vial adapter removably attached on the housing and detachable therefrom along a line of detachment co-directional with the device axis. The housing has three ports, a first port onto which is connected the source of physiological fluid, a second port which leads to the medicinal vessel, and a third port which is fitted with a drug dispenser such as a needle, an atomizer, and the like.

The inline liquid drug medical device includes a manually operated actuating mechanism for applying a linear displacement force to a flow control member sealingly accommodated inside a bore in the housing for sliding the flow control member along the bore in a transverse direction to the device axis from an initial first flow control position for liquid drug reconstitution purposes to a subsequent second flow control position for liquid drug administration purposes. The first flow control position enables flow communication between the first port and the second port for liquid drug reconstitution purposes. The second flow control position enables flow communication between the first port and the third port fitted with a drug dispenser such as a needle, an atomizer, and the like, for liquid drug administration purposes. The first and third ports are preferably co-axial for facilitating more intuitive use of the device.

The actuating mechanism has an initial liquid drug reconstitution position corresponding with the flow control member's first flow control position and a subsequent liquid drug administration position corresponding with the flow control member's second flow control position. One type of actuating mechanism employs a manual radial actuation force having a component for imparting a linear displacement force to the flow control member. Another type of actuating mechanism employs a manual linear actuation force for imparting a linear displacement force to a flow control member. Actuating mechanisms are preferably integrally formed with vial adapters for removal together with the vial adapters on detaching same from a housing after liquid drug reconstitution and prior to liquid drug administration. Alternatively, the actuating mechanisms can be integrally formed with the housings.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figure 1:
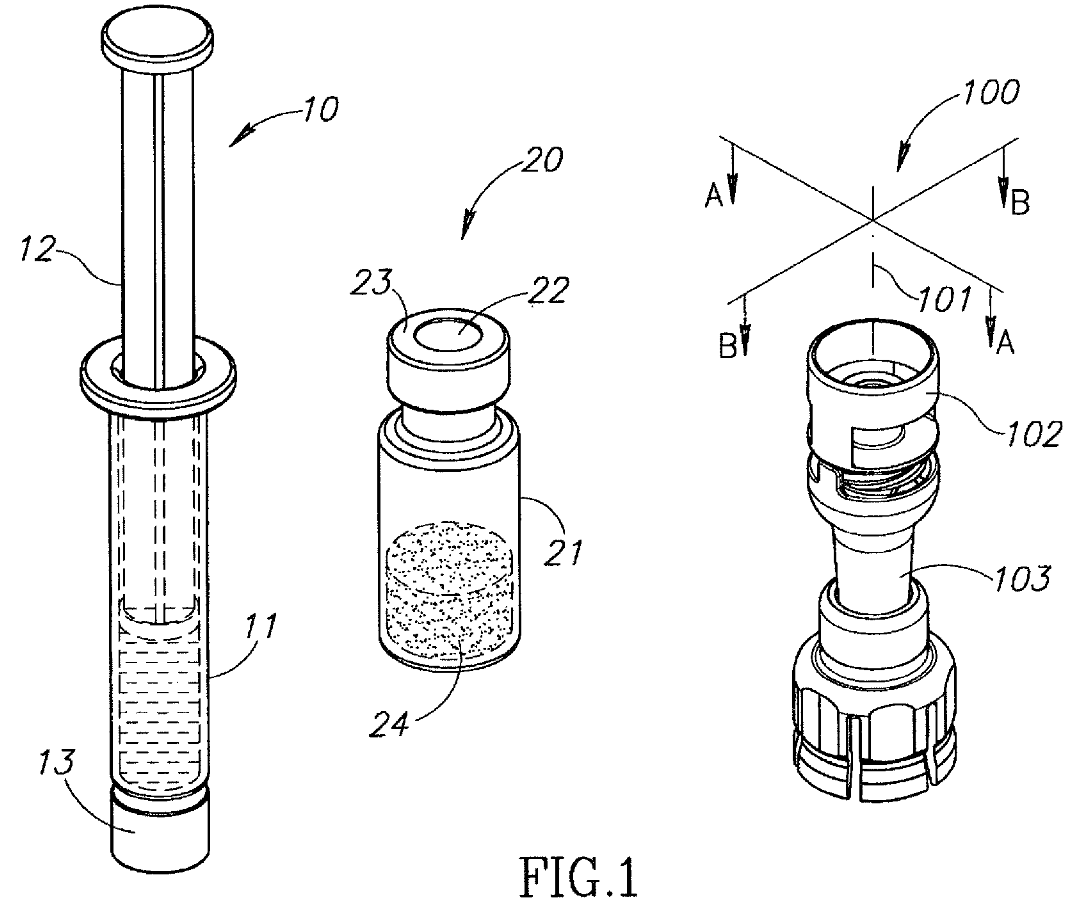
FIG. 1 is a pictorial representation of a syringe, a vial and an inline liquid drug medical device having a rotary actuating mechanism and a linear displaceable sliding flow control member.
Figure 2:
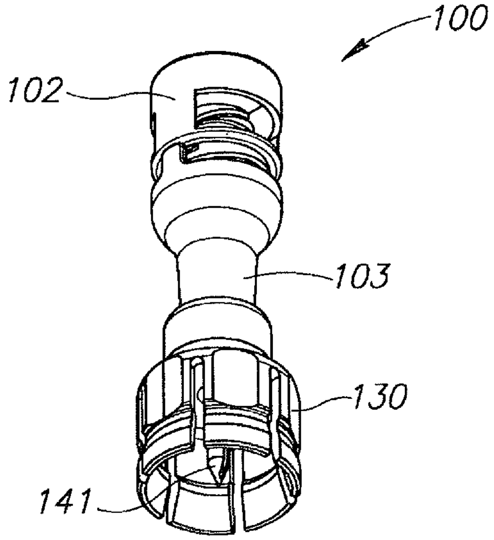
FIG. 2 is a bottom perspective view of FIG. 1's device.

Inline Liquid Drug Medical Device Including a Manually Operated Rotary Actuating Mechanism and a Linear Displaceable Sliding Flow Control Member FIG. 1 shows a syringe 10 constituting a source of physiological fluid, a vial 20 constituting a medicinal vessel and an inline liquid drug medical device 100 for use with the syringe 10 and the vial 20. The syringe 10 includes a barrel 11 with a plunger 12 and a male Luer lock connector 13. The syringe 10 can be formed with other types of connectors. The vial 20 includes an open topped bottle 21 sealed by a vial stopper 22 capped by a metal band 23 or other suitable capping material. The vial 20 contains either a powdered or liquid drug 24. The syringe 10 typically contains diluent for reconstituting the vial contents 24.

FIGS. 2 to 6 show the inline liquid drug medical device 100 having a longitudinal device axis 101 and including a housing 102 and a vial adapter 103 removably coupled on the housing 102 and detachable therefrom along a line of detachment co-directional with the device axis 101. The housing 102 includes a generally cylindrical body 104 coaxial with the device axis 101 and having a syringe port 108 at one end and a port manifold 109 at its opposing end. The body 104 includes a throughgoing bore 106 having a bore axis 107 transversely directed to the device axis 101, a proximal bore end 106A and a distal bore end 106B. The body 104 includes a threaded intermediate section 112 with circumferentially surrounding fastening threads 112A. An annular hand held sleeve 111 coaxially aligned with the device axis 101 is attached to the intermediate section 112 by two opposite attachment walls 118 for enabling a user to conformably grip the housing 102 during use. The sleeve 111 includes a sleeve opening 111A for allowing access to the syringe port 108.

The syringe port 108 constitutes a first port in flow communication with the bore 106. The syringe port 108 is intended to the syringe's connector 13 and is co-directional with the device axis 101 and preferably co-axial therewith. The syringe port 108 is typically in the form of a female Luer connector intended for receiving a syringe's male Luer lock connector. The port manifold 109 is generally cylindrically shaped and is coaxially aligned with the device axis 101. The port manifold 109 includes a second port 113 and a third port 114 both in flow communication with the bore 106. The second port 113 and the third port 114 are co-directional with the device axis 101 and the third port 114 is preferably co-axial therewith. The third port 114 is preferably fitted with a needle 116 for liquid drug administration purposes. The second port 113 is preferably recessed with respect to the third port 114 thereby forming an annular cavity 117 for removably coupling the vial adapter 103 on the housing 102.

The device 100 includes a linear displaceable sliding flow control member (FCM) 120 sealingly accommodated in the bore 106 for establishing flow communication between the syringe port 108 and the second port 113 in a first flow control position for liquid drug reconstitution purposes, and between the syringe port 108 and the third port 114 in a second flow control position for liquid drug administration purposes. The flow control member 120 is of a generally cylindrical shape and has a peripheral cylindrical surface 121 with a semi-circular peripheral flow channel 122 and a longitudinally directed flow cutout 123, a blind bore 124, a proximal FCM end 126, and a distal FCM end 127.

A proximal rounded protrusion 128 extends beyond the proximal FCM end 126, and serves as an abutment surface for applying a radial actuation force RAF thereagainst to impart a linear displacement force LDF to urge the flow control member 120 along the bore 106. In the first flow control position, the flow control member 120 is sealingly inserted in the bore 106 with the proximal rounded protrusion 128 substantially protruding out of the proximal bore end 106A (see FIGS. 5A-5D). In the second flow control position, the proximal rounded protrusion 128 is substantially wholly inserted in the proximal bore end 106A (see FIGS. 6A-6C).

The longitudinally directed flow cutout 123 is dimensioned so that it is in flow communication with the first port 108 when the flow control member 120 is in both its first flow control position and its second flow control position. The flow channel 122 is disposed towards the proximal FCM end 126 circumferentially extends from a proximal channel end 122A in flow communication with the flow cutout 123 to a distal channel end 122B. In the first flow control position, the distal channel end 122B is in flow communication with the second port 113 (see FIG. 5A), and in the second flow control position, the distal channel end 122B is in flow communication with the third port 114 (see FIG. 6A).

The vial adapter 103 includes a skirt 130 with a top surface 131 and downward depending flex members 132 for snap fitting onto the vial 20. The vial adapter 103 includes an elongated upright stem 133 and terminating in a circular stem end portion 134 having a stem cavity 135 shaped for accommodating onto the housing 102. The stem cavity 135 includes an upper body cavity section 135A for rotatably fitting onto the generally cylindrical body 104 and a cylindrically shaped lower manifold cavity section 135B for rotatably fitting onto the port manifold 109.

The stem 133 includes an annular manifold support 136 at a distal end of the lower manifold cavity section 135B for circumferentially coupling with the annular cavity 117. A fluid conduit 137 which is co-axial with the device axis 101 has a proximal end 137A in the annular manifold support 136 for sealed flow communication with the second port 113 on coupling the vial adapter 103 to the housing 102. The fluid conduit 137 fluidly connects at a distal end 137B to a co-axial puncturing cannula 141 through a fluid interconnect conduit 137C. The puncturing cannula 141 serves to puncture the vial stopper 22 on its positive insertion into the vial adapter 103, and extends slightly therebeyond so that on inverting the vial 20 its nearly entire contents 24 can be aspirated therefrom through the puncturing cannula 141 to syringe 10. The stem 133 also includes a blind needle bore 138 for receiving the needle 116 on coupling the vial adapter 103 on the housing 102.

Figure 3A:
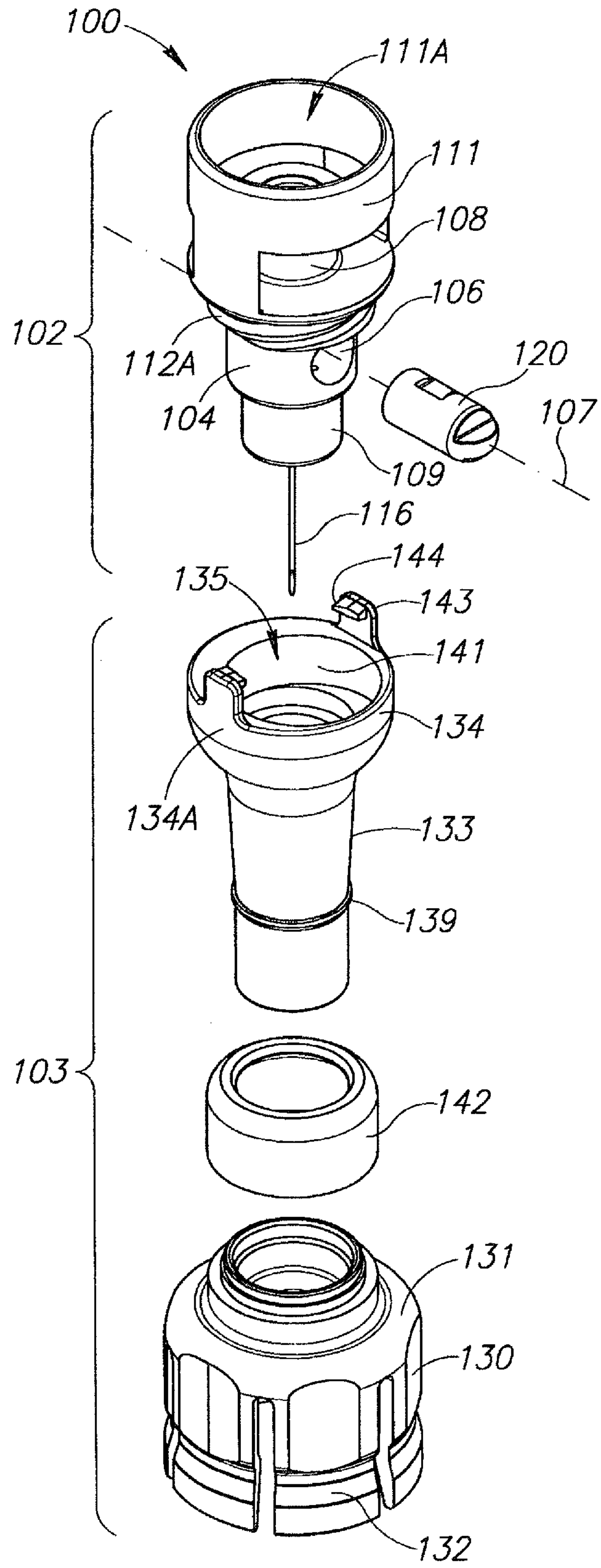
FIG. 3A is a partially exploded view of FIG. 1's device.
Figure 3B:
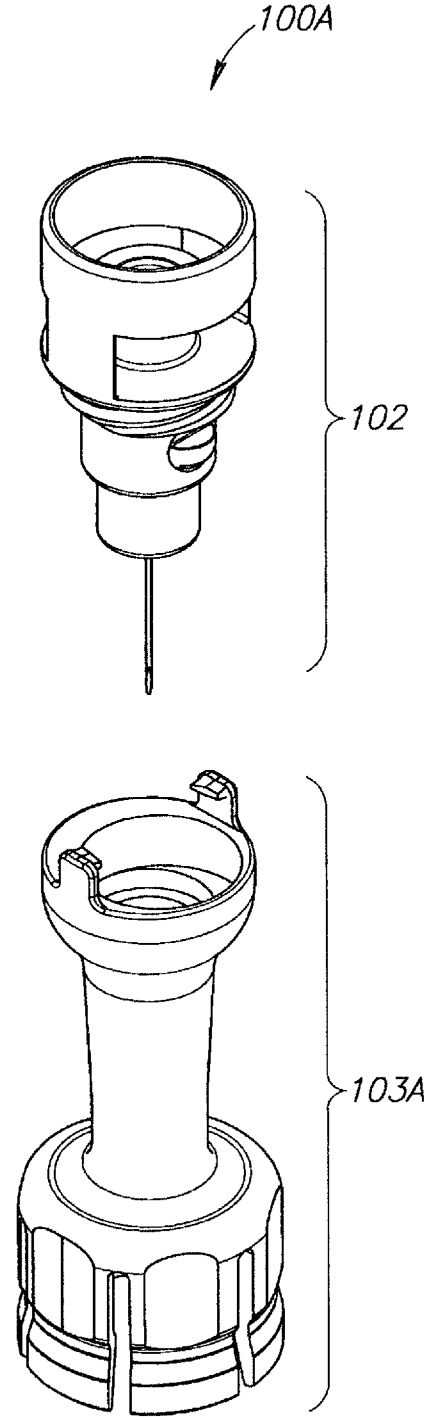
FIG. 3B is a partially exploded view of another embodiment of FIG. 1's device with an integral vial adapter.
Figure 4A:
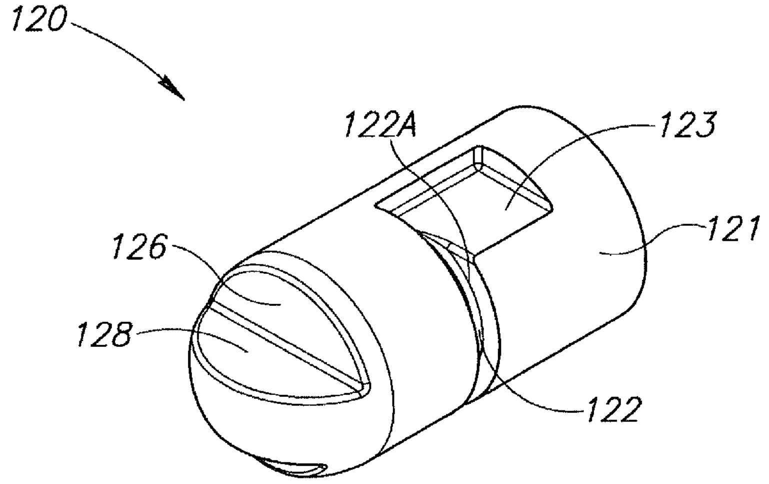
FIG. 4A is a top perspective view of FIG. 1's device's flow control member.
Figure 4B:
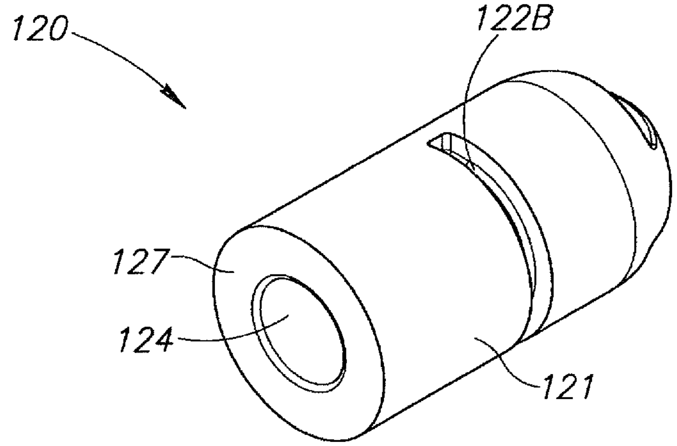
FIG. 4B is a bottom perspective view of FIG. 1's device's flow control member.
Figure 5A:
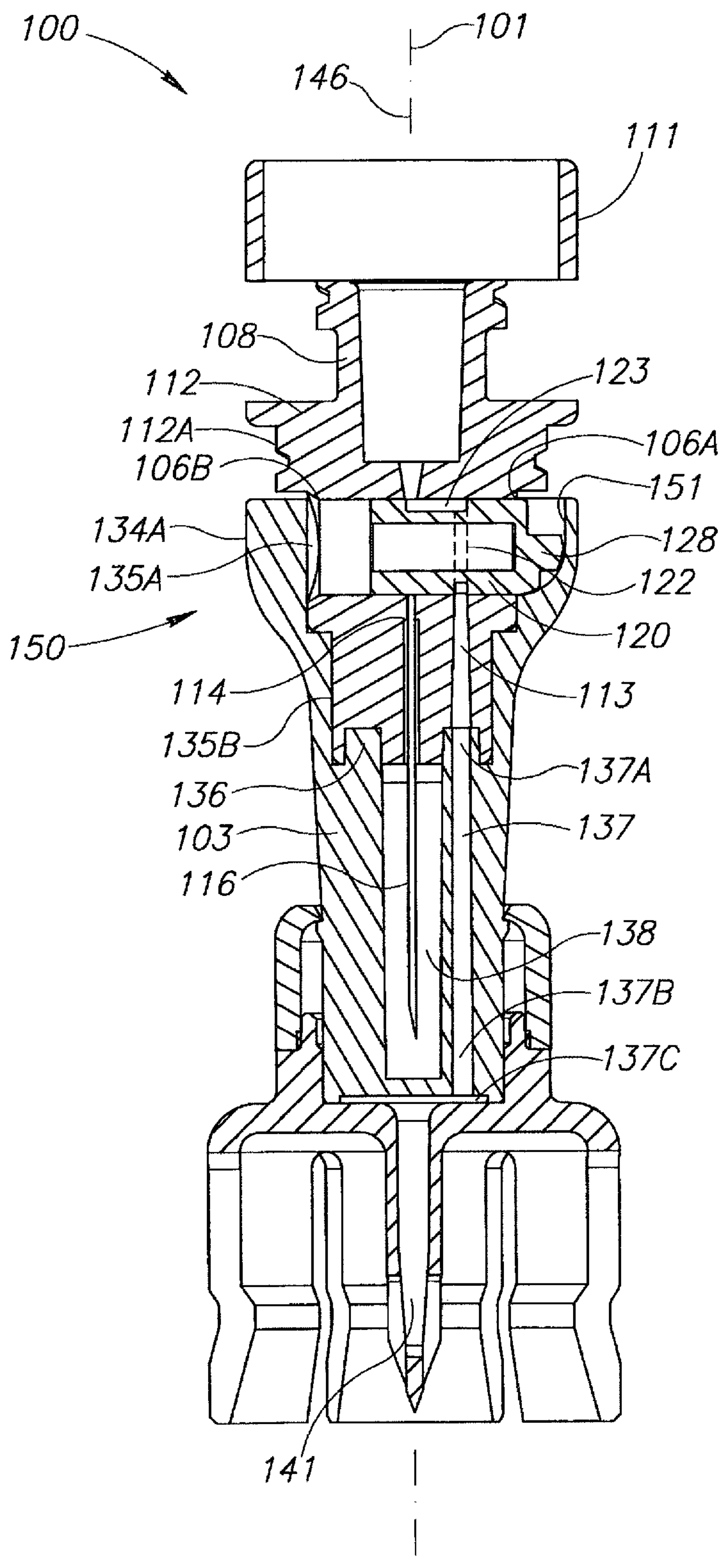
FIGS. 5A and 5B are longitudinal cross sections of FIG. 1's device along lines A-A and B-B, respectively, in FIG. 1 showing its actuating mechanism in an initial liquid drug reconstitution position and its flow control member in a first flow control position for liquid drug reconstitution purposes.
Figure 5B:
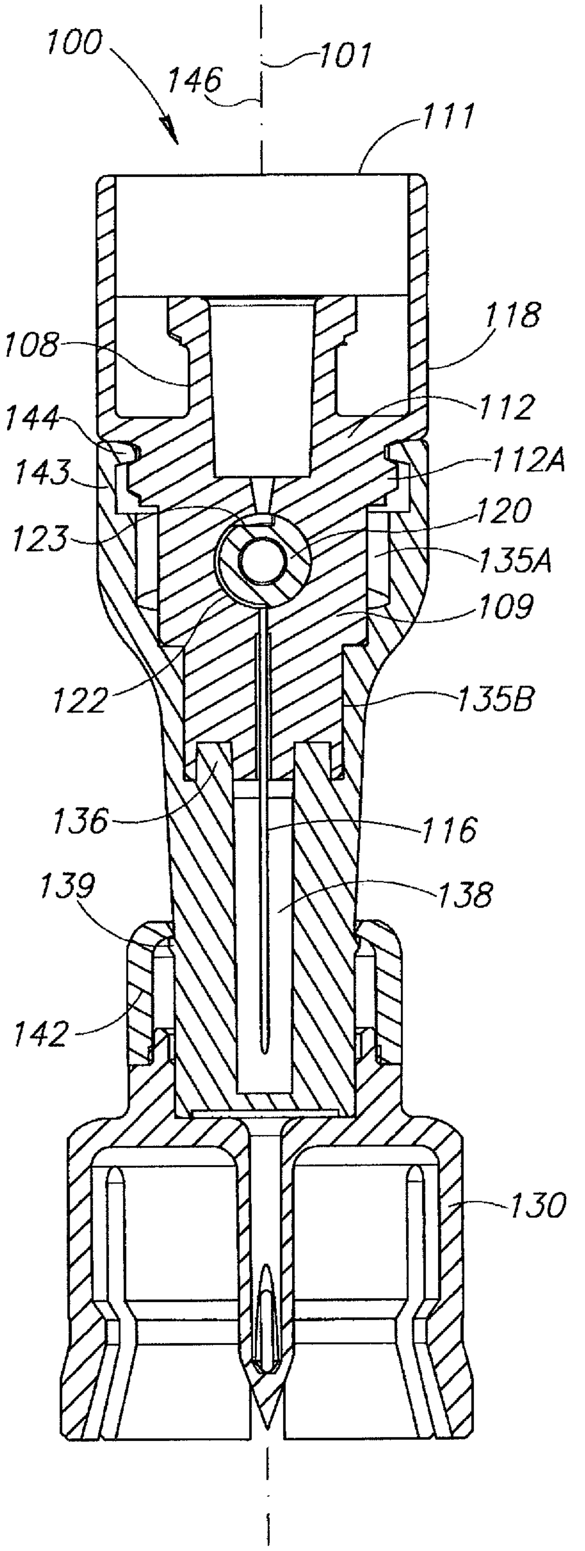
Figure 5C:
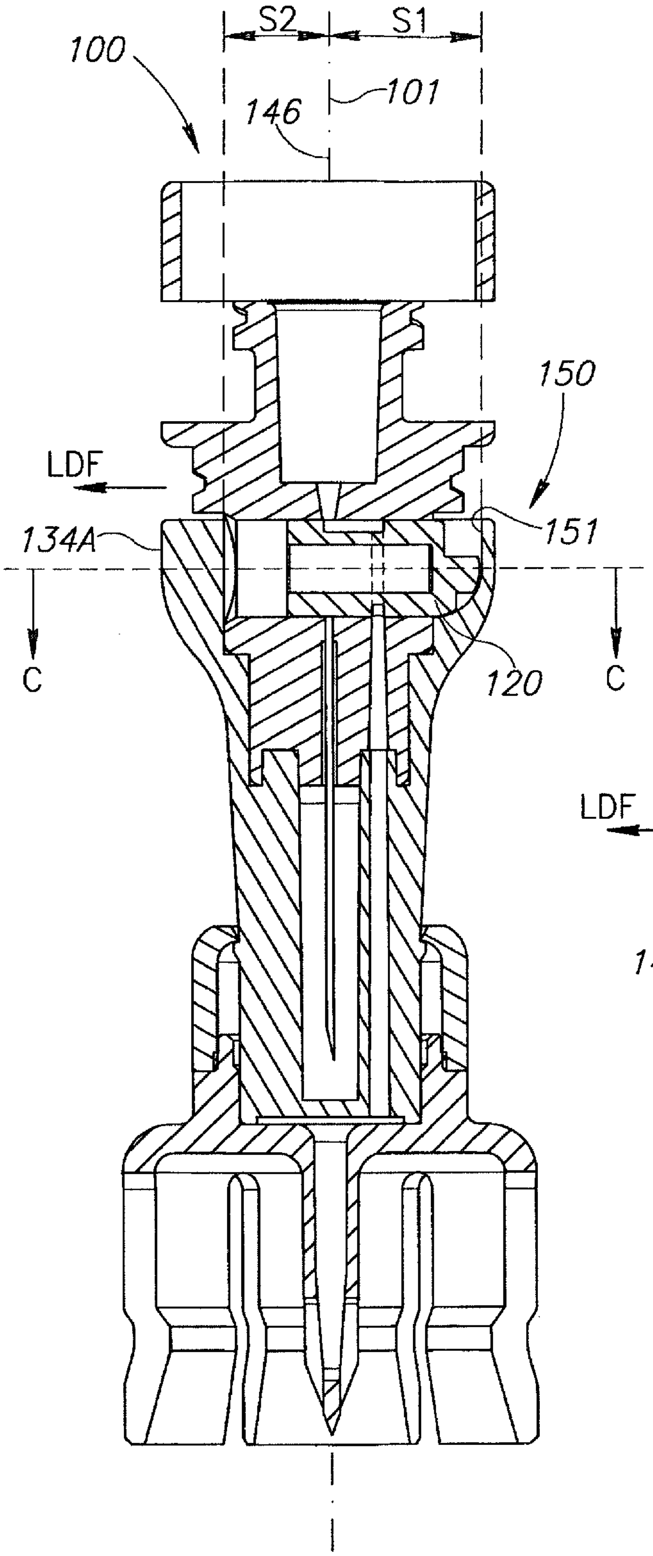
FIG. 5C is similar to FIG. 5A showing the separation distances S1 and S2 between opposite internal surfaces of the actuating mechanism relative to its axis of rotation.
Figure 5D:
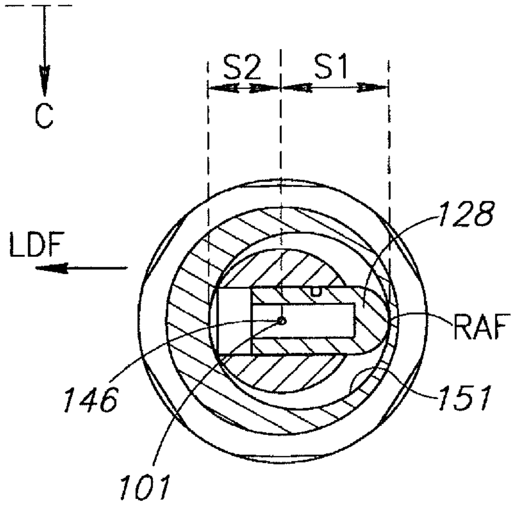
FIG. 5D is a transverse cross section of FIG. 1's device along line C-C in FIG. 5C showing the separation distances S1 and S2 between opposite internal surfaces of the actuating mechanism relative to its axis of rotation.

In a first embodiment, as shown in FIG. 3A, the stem 133 has a circumferential rim 139 along a bottom section for engaging a coupler 142 which secures the stem 133 to the top surface 131. In another embodiment, as shown in FIG. 3B, a device 100A similar to device 100 includes an integrally built vial adapter 103A which is removably coupled to the housing 102.

The vial adapter 103 is screw threaded onto the housing 102 by means of a pair of opposite fastening members 143 extending upright from the stem end portion 134 co-directional and on opposing sides of the device axis 101. The fastening members 143 each have a perpendicularly projecting tooth 144 for engaging the fastening threads 112A. As the vial adapter 103 is rotated relative to the housing 102 about an axis of rotation 146 co-axial with the device axis 101, the vial adapter 103 unscrews from the housing 102 and is detachable therefrom along a line of detachment co-directional with the device axis 101.

The vial adapter 103 is integrally formed with a manually operated rotary actuating mechanism 150 for applying a radial actuation force RAF for imparting a linear displacement force LDF for sliding the flow control member 120 along the bore 106 from its first flow control position to its second flow control position. The actuating mechanism 150 is implemented by employing a semi-circular internal cam surface 151 of the stem end portion 134 for bearing against the proximal rounded protrusion 128 as the vial adapter 103 is rotationally detached from the housing 102. The actuating mechanism 150 has an initial liquid drug reconstitution position corresponding to the flow control member 120's first flow control position when the vial adapter 103 is screw threaded attached on the housing 102 and a subsequent liquid drug administration position corresponding with the flow control member 120's second flow control position when the vial adapter 103 is detachable from the housing 102. The internal cam surface 151 defines a separation (S) relative to the axis of rotation 146. The internal cam surface 151 has a maximum separation S1 at the actuating mechanism 150's liquid drug reconstitution position and a minimum separation S2 in actuating mechanism 150's liquid drug administration position. The separation S2 is smaller than the separation S1 such that as the vial adapter 103 is screw unthreaded from the housing 102, the internal cam surface 151 applies a radial actuation force RAF against the protrusion 128 having a component for imparting a linear displacement force (LDF) to the flow control member 120 for sliding same along the bore 106 from its first flow control position to its second flow control position. The stem end portion 134 has an external surface 134A with a uniform radius relative to the axis of rotation 146 such that its wall thickness increases from its thinnest where the internal cam surface 151 abuts the flow control member 120 at the actuating mechanism's liquid drug reconstitution position to its thickest where the internal cam surface 151 abuts the flow control member 120 at the actuating mechanism's liquid drug administration position.

Operation of the device 100 may best be explained by referring to FIGS. 5A-5D and FIGS. 6A-6C.

FIGS. 5A-5D show the actuating mechanism 150 in its initial liquid drug reconstitution position and the flow control member 120 in its first flow control position. The vial adapter 103 is screw threaded onto the housing 102 and the flow control member 120 protrudes from the proximal bore end 106A with the proximal rounded protrusion 128 abutting the internal cam surface 151.

Figure 6A:
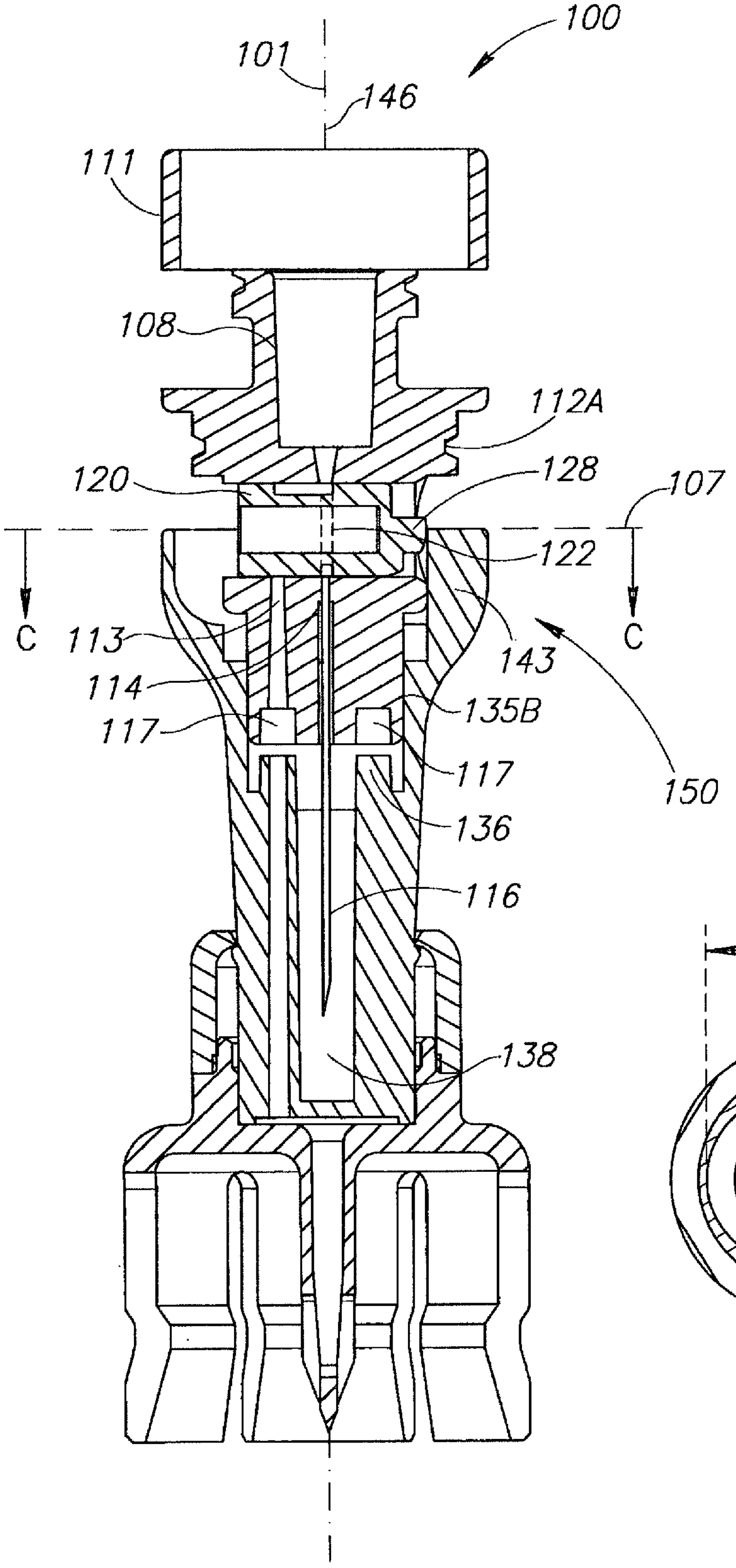
FIG. 6A is a longitudinal cross section of FIG. 1's device along line A-A in FIG. 1 showing its actuating mechanism in a subsequent liquid drug administration position and its flow control member in a second flow control position for liquid drug administration purposes.
Figure 6B:
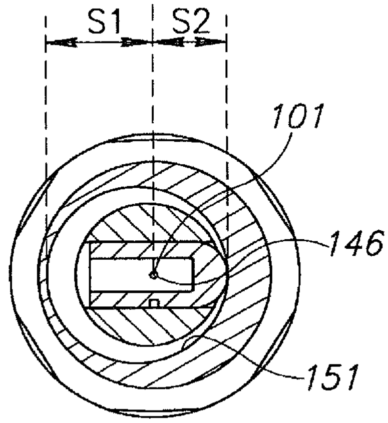
FIG. 6B is a transverse cross section of FIG. 1's device along line C-C in FIG. 6A showing its actuating mechanism in its subsequent liquid drug administration position and its flow control member in its second flow control position for liquid drug administration purposes.
Figure 6C:
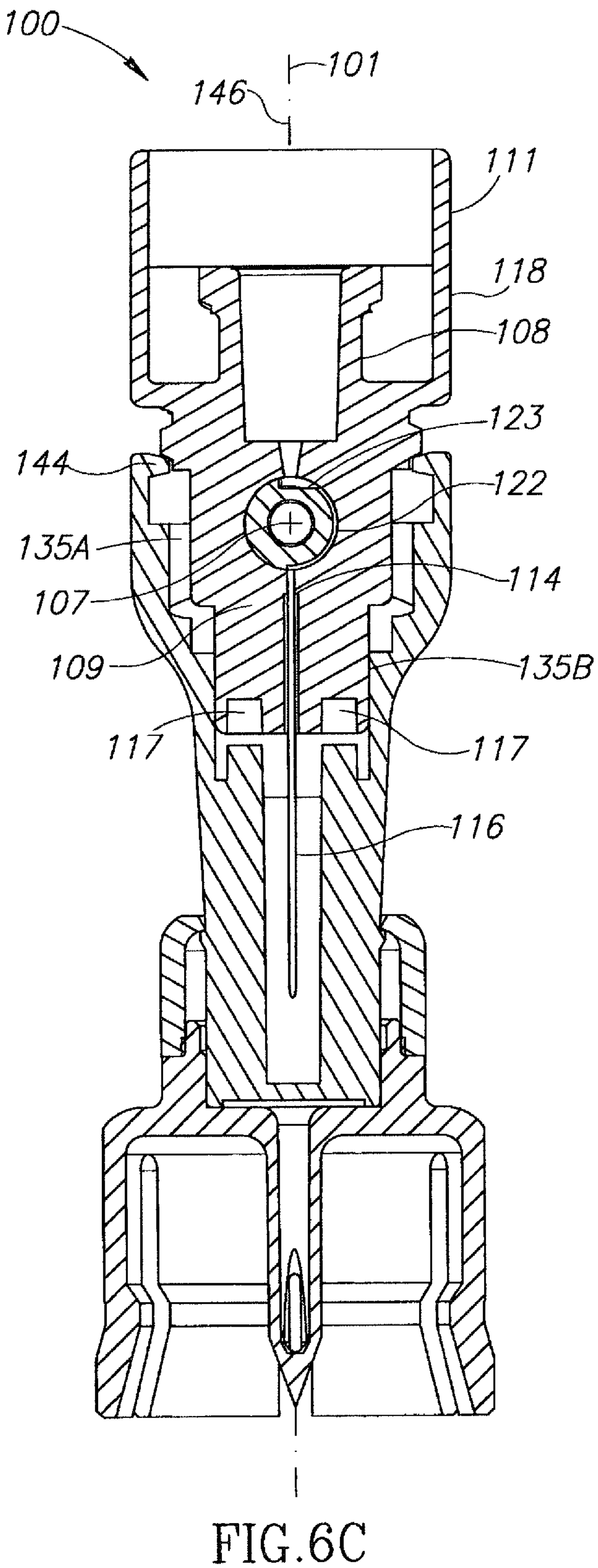
FIG. 6C is a longitudinal cross section of FIG. 1's device along line B-B in FIG. 1 showing its actuating mechanism in its liquid drug administration position and its flow control member in its second flow control position for liquid drug administration purposes.

FIGS. 6A-6C show the actuating mechanism 150 in its subsequent liquid drug administration position and the flow control member 120 in its second flow control position after a half turn unthreading the vial adapter 103 from the housing 102. The radial actuation force RAF is continuously applied to the flow control member 120 by the internal cam surface 151 having a continuously decreasing separation S from the axis of rotation 146 for imparting the linear displacement force LDF to slidingly displace the flow control member 120 to its second flow control position. The teeth 144 fully disengage from the fastening threads 112A at the actuating mechanism's liquid drug administration position when the flow control member 120 is in the second flow control position at which time the vial adapter 103 is detachable from the housing 102.

Figure 7A:
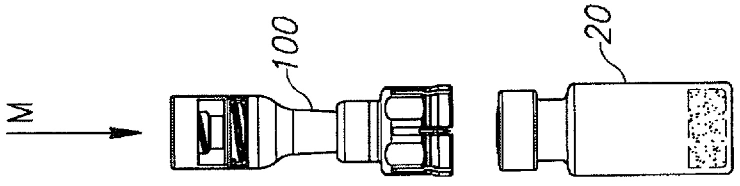
FIGS. 7A to 7G show the use of FIG. 1's device for liquid drug reconstitution and administration purposes.

The use of the inline liquid drug medical device 100 for liquid drug reconstitution and administration is shown in FIGS. 7A to 7G as follows:

FIG. 7A shows the device 100 is in its initial first flow control position for liquid drug reconstitution and a user mounting the device 100 on a vial 20, as indicated by arrow M.

Figure 7B:
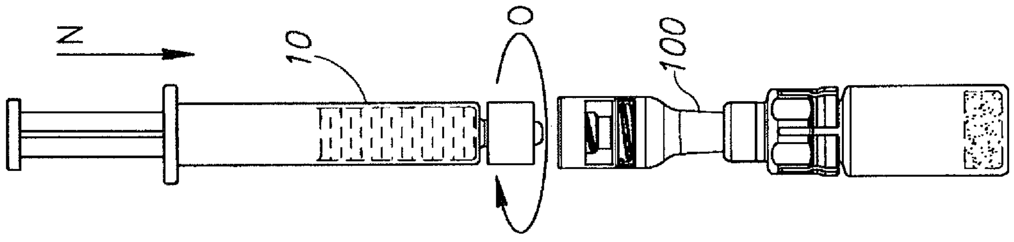

FIG. 7B shows the user approximating the syringe 10 towards the device 100, as indicated by arrow N, and screw threading the syringe 10 onto the device 100, as indicated by arrow O.

Figure 7C:
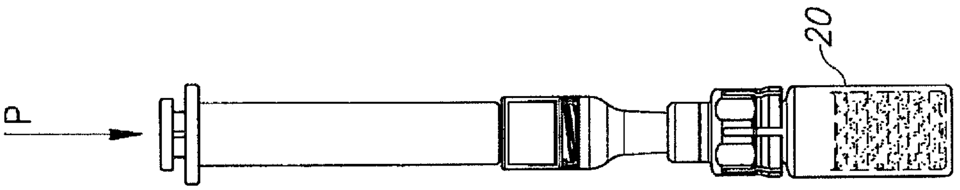

FIG. 7C shows the user injecting the syringe's contents into the vial 20, as indicated by arrow P. The user agitates the assemblage for reconstituting the liquid drug.

Figure 7D:
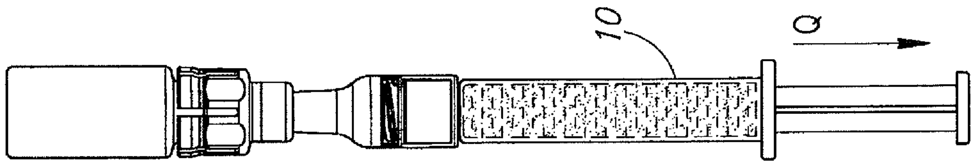

FIG. 7D shows the user inverting the assemblage and aspirating the reconstituted liquid drug contents into the syringe 10, as indicated by arrow Q.

Figure 7G:
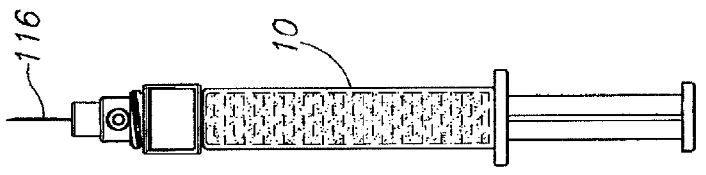
Figure 7F:
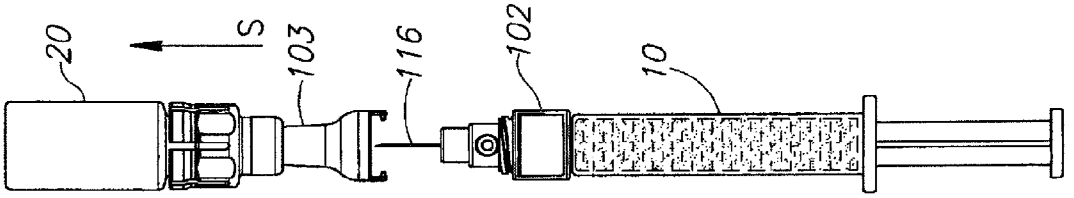
Figure 7E:
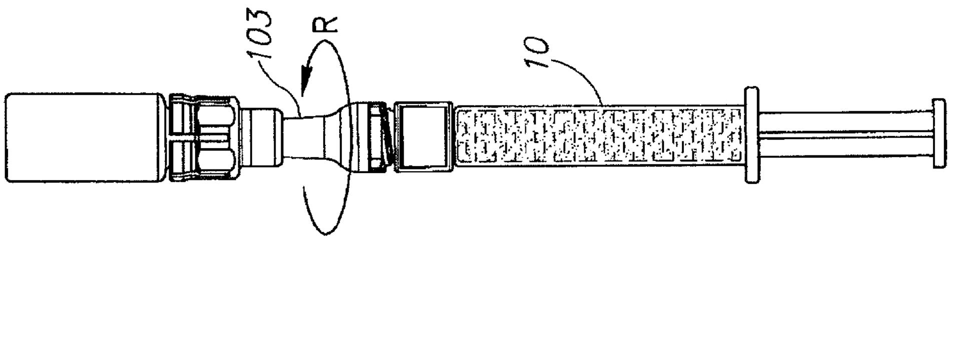

FIG. 7E shows the user rotating the vial adapter 103 to the subsequent liquid drug administration position for slidingly displacing the flow control member 120 to its subsequent second flow control position, as indicated by arrow R. Optionally, for this step and the following steps, the user inverts the assemblage so that the syringe 10 is above the vial 20.

FIG. 7F shows the user screw threading the vial adapter 103 from the housing 102, as indicated by arrow S for exposing the needle 116, thereby enabling administration of the liquid drug (see FIG. 7G). The user disposes of the vial adapter 103 with the spent vial 20.

Figure 8:
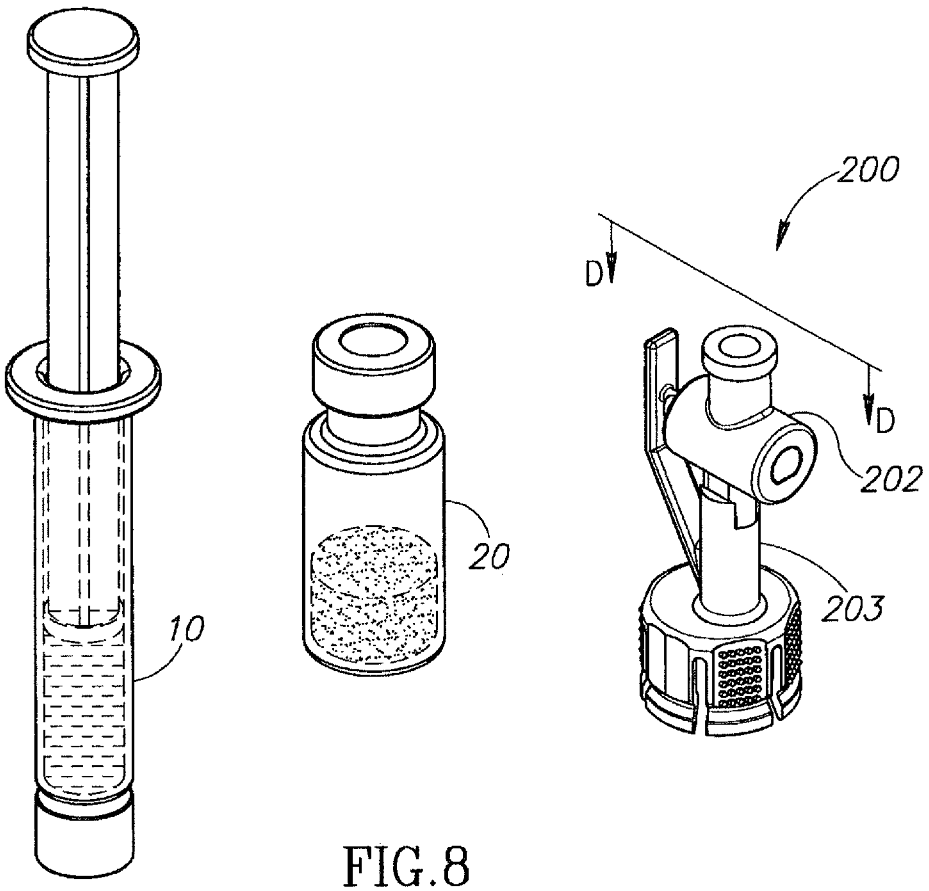
FIG. 8 is a pictorial representation of a syringe, a vial and an inline liquid drug medical device having an actuating mechanism with a spring leaf like actuator, and a linear displaceable sliding flow control member.
Figure 9:
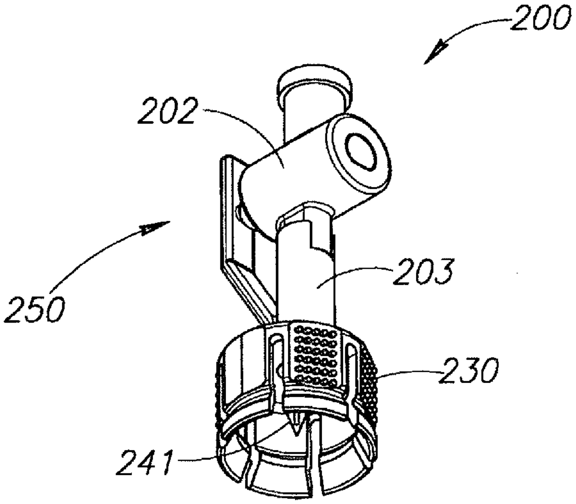
FIG. 9 is a bottom perspective view of FIG. 8's device.
Figure 10:
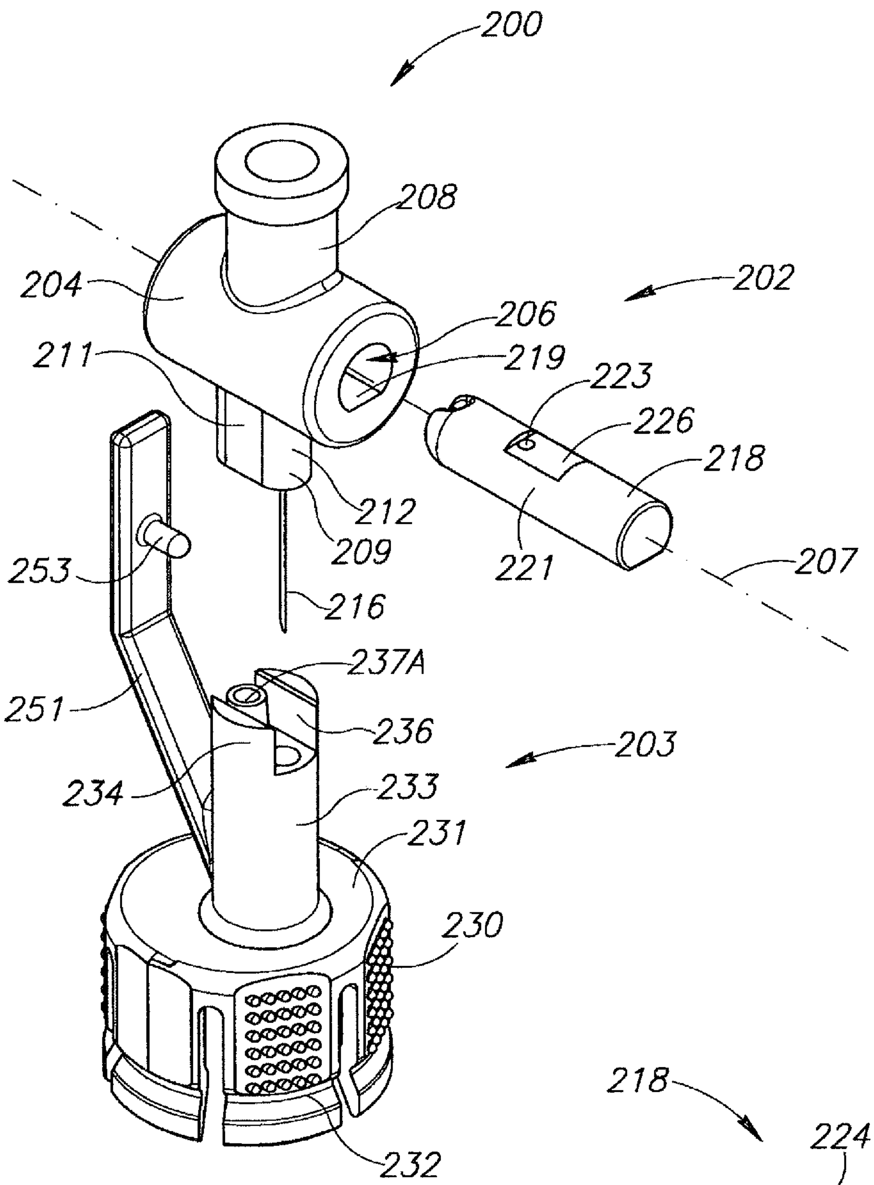
FIG. 10 is a partially exploded view of FIG. 8's device.
Figure 11:
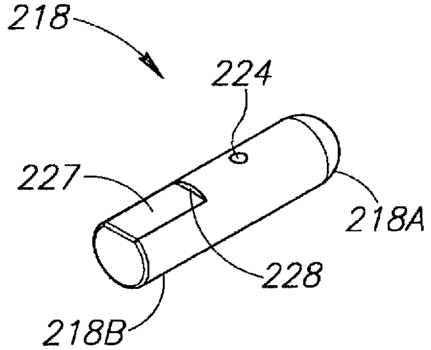
FIG. 11 is a top perspective view of FIG. 8's device's flow control member.
Figure 12:
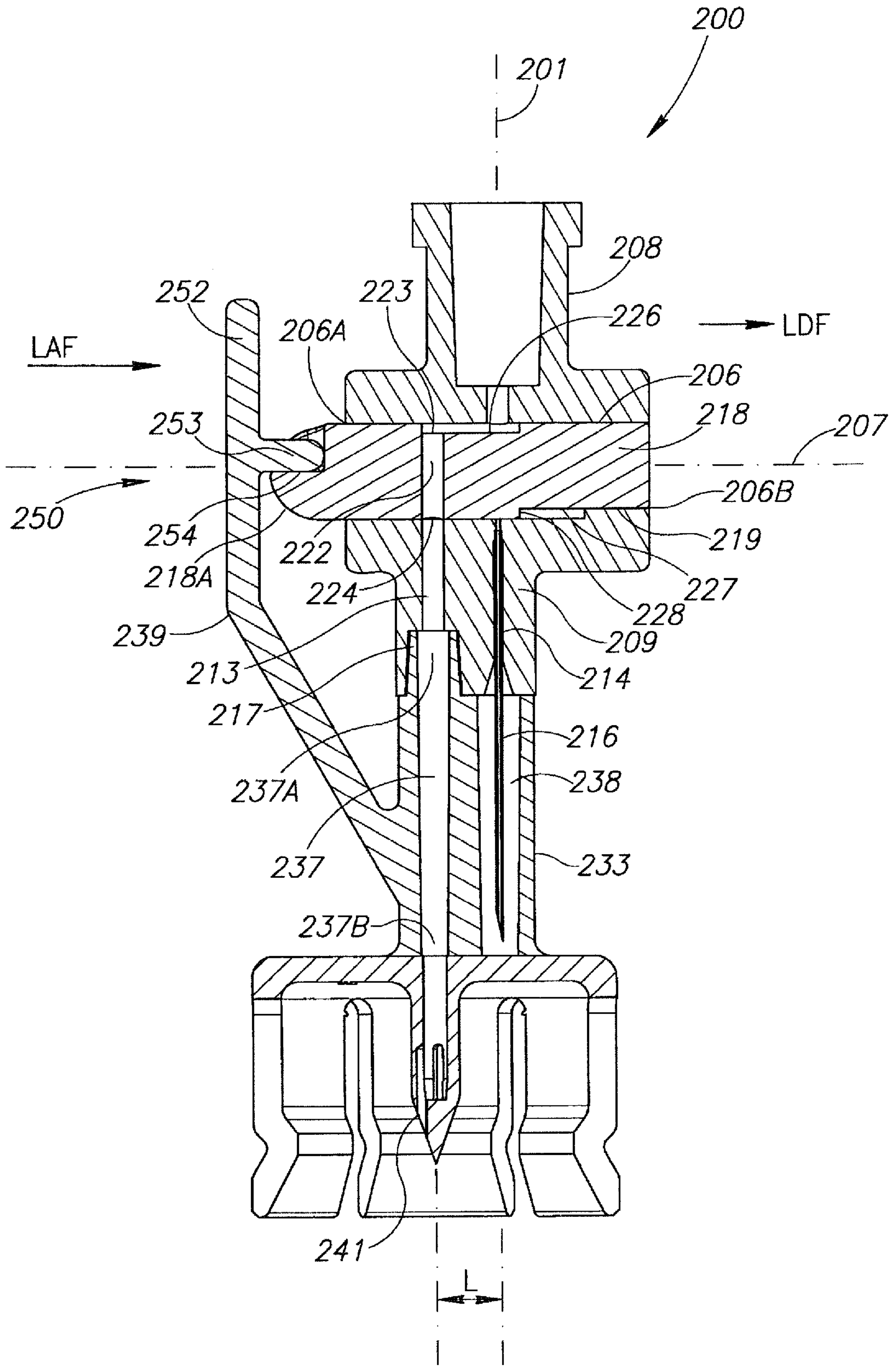
FIG. 12 is a longitudinal cross section of FIG. 8's device along line D-D in FIG. 8 showing its actuating mechanism in an initial liquid drug reconstitution position and its flow control member in a first flow control position for liquid drug reconstitution purposes.
Figure 13:
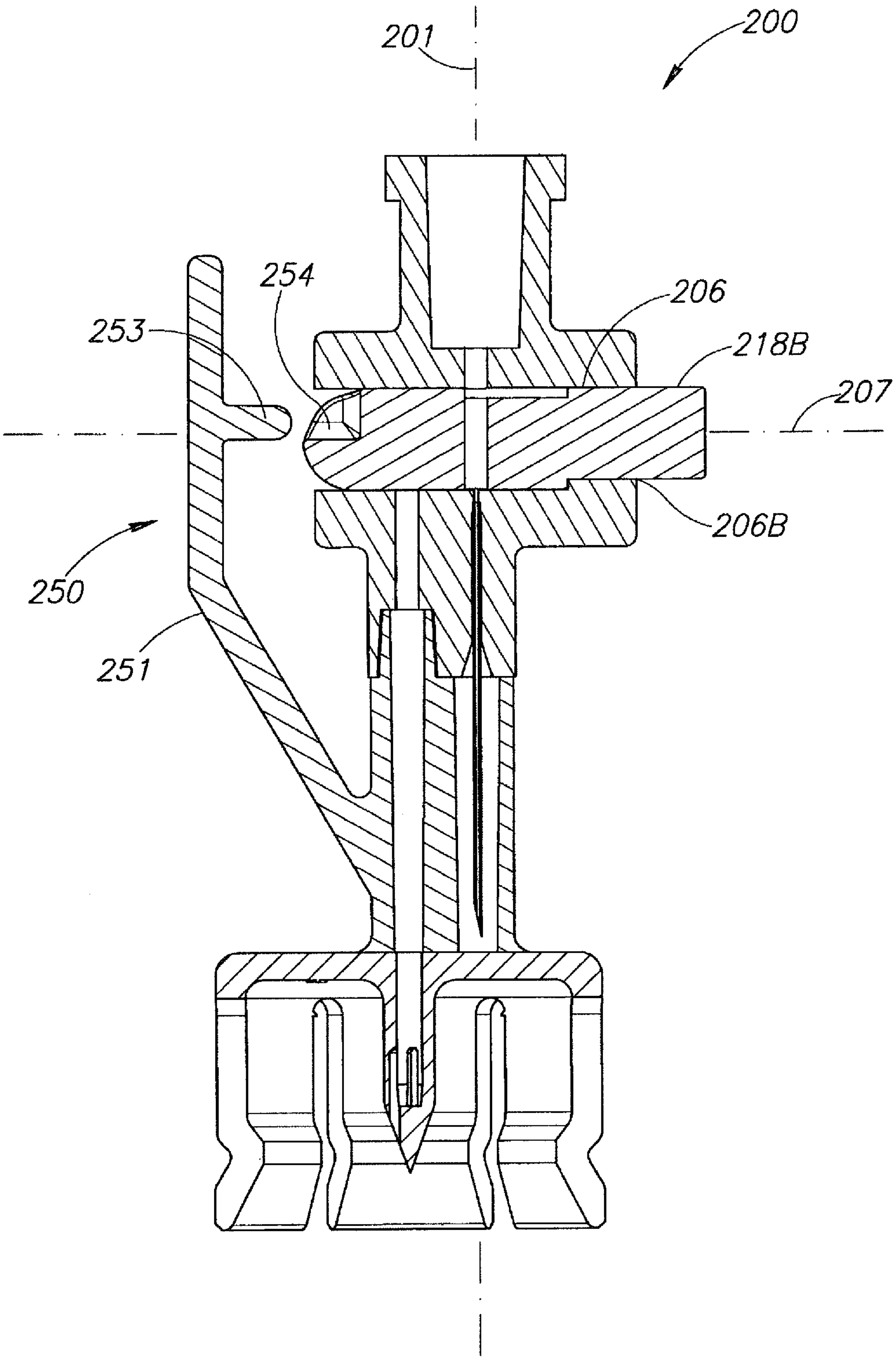
FIG. 13 is a longitudinal cross sections of FIG. 8's device along line D-D in FIG. 8 showing its flow control member in a second flow control position for liquid drug administration purposes subsequent to actuation of its actuating mechanism.

Inline Liquid Drug Medical Devices Including a Manually Operated Actuating Mechanism with a Spring Leaf-Like Actuator and a Linear Displaceable Sliding Flow Control Member FIG. 8 shows the syringe 10, the vial 20 and an inline liquid drug medical device 200 for use with the syringe 10 and the vial 20.

FIGS. 9 to 13 show the inline liquid drug medical device 200 has a longitudinal device axis 201 and includes a housing 202 and a vial adapter 203 removably coupled on the housing 202 and detachable therefrom along a line of detachment co-directional with the device axis 201. The housing 202 includes a generally cylindrical central body 204 with a throughgoing bore 206 having a bore axis 207 transversely directed to the device axis 201 and having a proximal end 206A and a distal end 206B.

The housing 202 includes a syringe port 208 constituting a first port in flow communication with the bore 206 and a port manifold 209 on opposite sides of the central body 204. The syringe port 208 is co-directional with the device axis 201 and preferably co-axial therewith. The port manifold 209 includes a pair of opposite and parallel major surfaces 211 co-directional with the bore axis 207 and a pair of opposite minor end surfaces 212 for securing the vial adapter 203 onto the housing 202. The port manifold 209 includes the second port 213 and the third port 214 both in flow communication with the bore 206. The second port 213 and the third port 214 are co-directional with the device axis 201 and the third port 214 is preferably co-axial therewith. A center of the second port 213 is offset from the device axis 201 by a length L. The third port 214 is preferably fitted with a needle 216. The second port 213 is preferably recessed with respect to the third port 214 thereby forming a cavity 217 for sealingly coupling the vial adapter 203 to the housing 202.

The housing 202 includes a flow control member 218 for sliding linear movement along the bore 206 from an initial first flow control position for establishing flow communication between the first port 208 and the second port 213 to a subsequent second flow control position for establishing flow communication between the first port 208 and the third port 214. The bore 206 has a uniform cross section therealong except its distal end 206B which is formed with a platform 219 on the side of the port manifold 209 for acting as a stopper for stopping the sliding linear movement of the flow control member 218 at its second flow control position. The platform may be formed on the side of the syringe port 208.

The flow control member 218 has a proximal end 218A and a distal end 218E and a peripheral cylindrical surface 221. The flow control member 218 is shaped and dimensioned for sealing insertion in the throughgoing bore 206 and is longer than same such that its proximal end 218A protrudes from the proximal end 206A in its first flow control position (see FIG. 12) and its distal end 218B protrudes from the distal end 206B in its second flow control position (see FIG. 13).

The flow control member 218 includes a flow channel 222 co-directional with the device axis 201 and disposed toward the proximal end 218A. The flow channel 222 has a proximal end 223 and a distal end 224. The peripheral surface 221 is formed with a longitudinally directed flow cutout 226 and a second longitudinally directed cutout 227 on the opposite side to the flow cutout 226. The cutout 227 faces the port manifold 209 and is located towards the distal end 218B and defines an abutment surface 228 for abutting against the stopper 219 for stopping the flow control member 218 at its second flow control position.

The vial adapter 203 includes a skirt 230 with a top surface 231 and downward depending flex members 232 for snap fitting onto a vial 20. The vial adapter 203 includes an elongated upright stem 233 terminating in a bifurcated tip 234 with a pair of opposite and parallel spaced apart inside surfaces 236 for friction fitting onto the port manifold 209's major surfaces 211. The stem 233 includes a fluid conduit 237 with a proximal end 237A for sealing insertion in the cavity 217 for sealed flow communication with the second port 213 on coupling the vial adapter 203 on the housing 202. The fluid conduit 237 terminates at the distal end 237B fluidly connecting with a pointed cannula 241. The stem 233 also includes a blind needle bore 238 for receiving the needle 216 on coupling the vial adapter 203 to the housing 202.

The vial adapter 203 is integrally formed with a manually operated actuating mechanism 250 for applying a linear actuation force LAF for imparting a linear displacement force LDF for sliding the flow control member 218 along the bore 206 from its first flow control position to its second flow control position. The actuating mechanism 250 is in the form of a hand operated upright spring leaf like actuator 251 attached towards the stem 233's base and having a free end 252 disposed opposite the flow control member's proximal end 218A. The actuator 251 has a pin 253 for sliding insertion into a recess 254 formed in the flow control member's proximal end 218A. The actuator 251 is preferably resiliently flexed from an initial position juxtaposed against the flow control member 218. The actuating mechanism 250 is preferably designed such that the pin 253 slides freely from the recess 254 on being released after being used to urge the flow control member 218 to its second flow control position to revert to its initial vertical position.

Figure 14D:
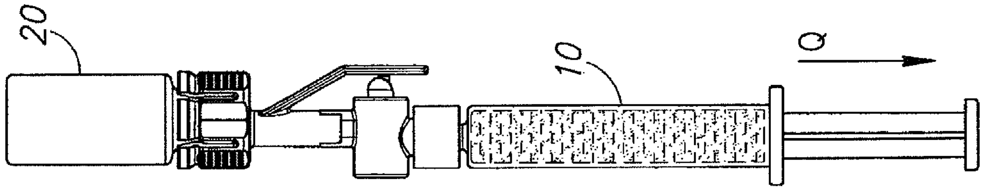
FIGS. 14A to 14H show the use of FIG. 8's device for liquid drug reconstitution and administration purposes.
Figure 14C:
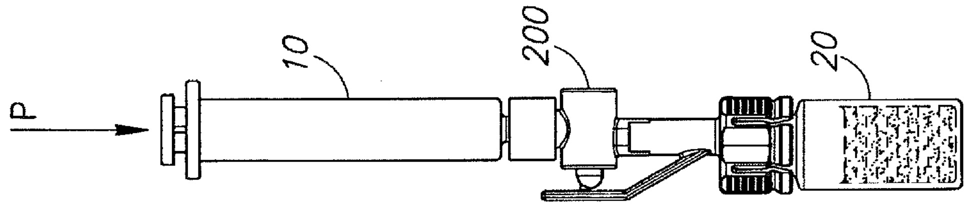
Figure 14B:
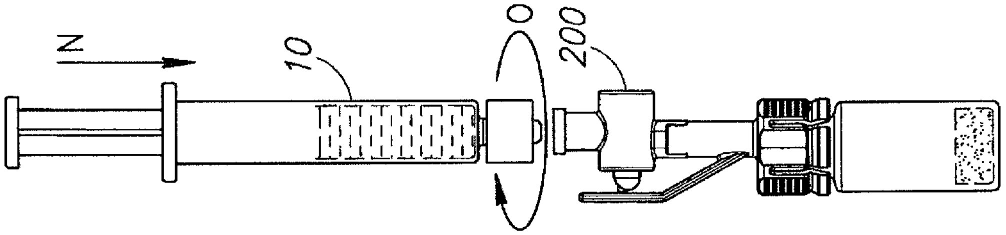
Figure 14A:
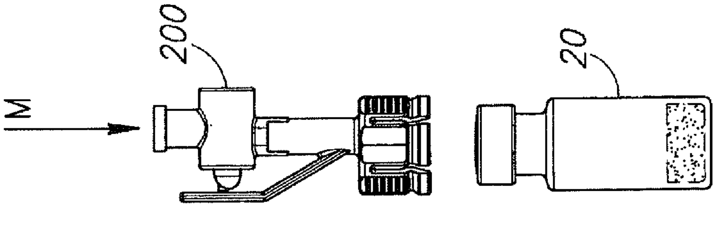

The use of the inline liquid drug medical device 200 for liquid drug reconstitution and administration as shown in FIGS. 14A to 14H is as follows:

FIG. 14A shows the device 200 is in its initial first flow control position for liquid drug reconstitution and a user mounting the device 200 on a vial 20, as indicated by arrow M.

FIG. 14B shows the user approximating the syringe 10 towards the device 200, as indicated by arrow N, and screw threading the syringe 10 onto the device 200, as indicated by arrow O.

FIG. 14C shows the user injecting the syringe's contents into the vial 20, as indicated by arrow P. The user agitates the assemblage for reconstituting the liquid drug.

FIG. 14D shows the user inverting the assemblage and aspirating the reconstituted liquid drug contents into the syringe 10, as indicated by arrow Q.

Figure 14E:
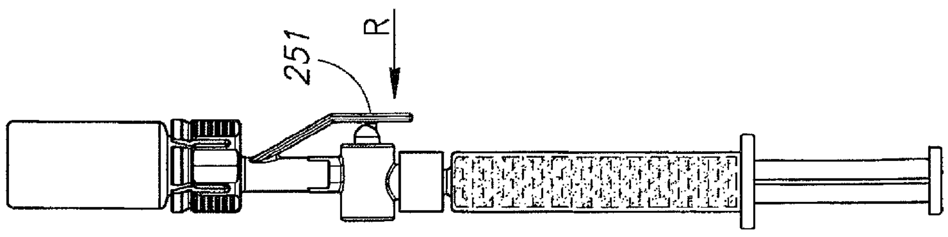

FIG. 14E shows the user depressing the hand operated actuator 239 to urge the flow control member 218 to its subsequent second flow control position in which the syringe port 208 is in flow communication with the third port 214, as indicated by arrow R.

Figure 14F:
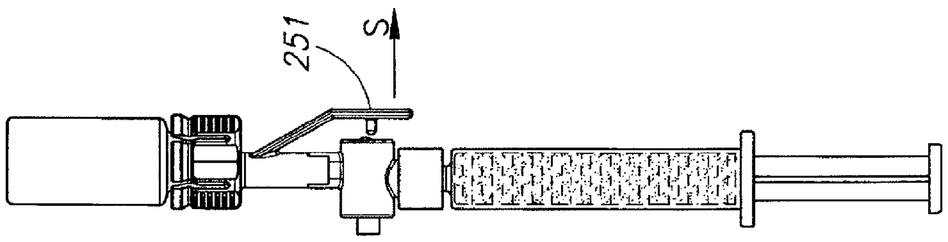

FIG. 14F shows the user releasing the hand operated actuator 251 which reverts to its pre-depressed position, as indicated by arrow S. Optionally, for this step and the following steps, the user inverts the assemblage so that the syringe 10 is up and the vial 20 is down.

Figure 14G:
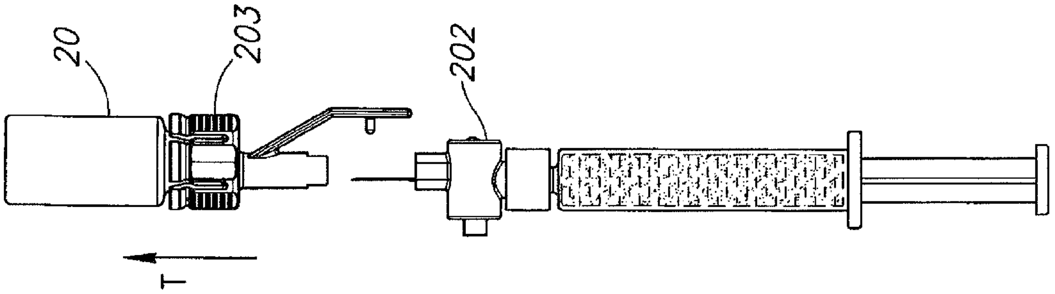
Figure 14H:
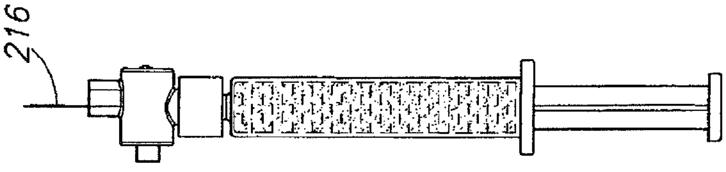

FIG. 14G shows the user pulling the vial adapter 203 with the spent vial 20 from the housing 202 for exposing the needle 216, as indicated by arrow T, thereby enabling administration of the liquid drug (see FIG. 14H).

Figure 15:
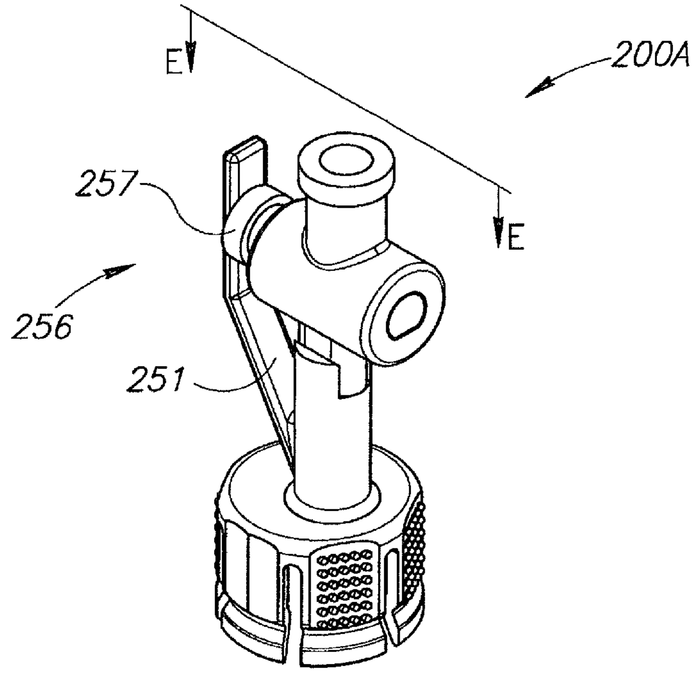
FIG. 15 is a pictorial representation of another embodiment of FIG. 8's device including a linear displaceable sliding flow control member in a first flow control position for liquid drug reconstitution purposes.
Figure 16:
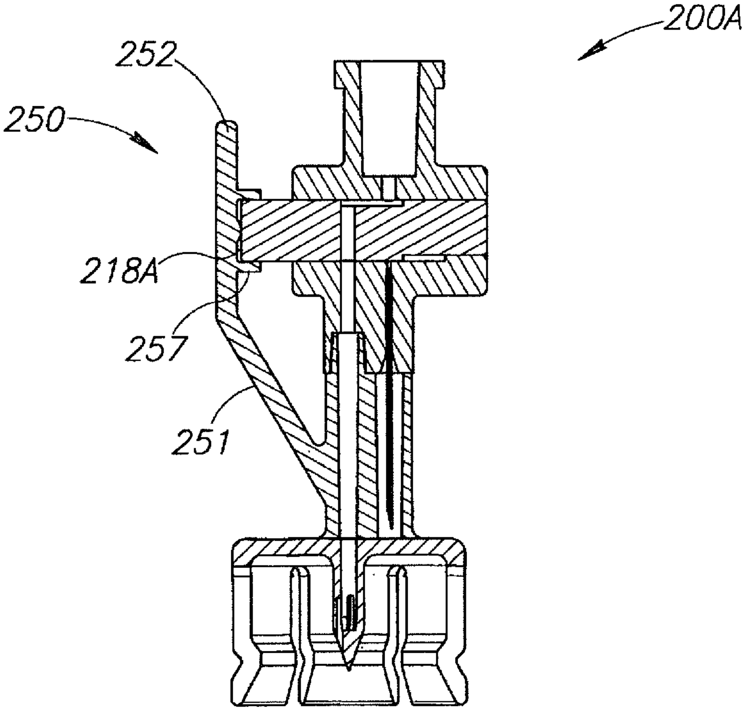
FIG. 16 is a longitudinal cross section of FIG. 15's device along line E-E in FIG. 15.

FIGS. 15 and 16 show an inline liquid drug medical device 200A similar in construction to the device 200 and therefore similar parts are likewise numbered. The device 200A differs from the device 200 insofar the former 200A includes an engagement mechanism 256 in which the free end 252 is formed with an annular flange 257 for engaging the proximal end 218A.

Figure 17:
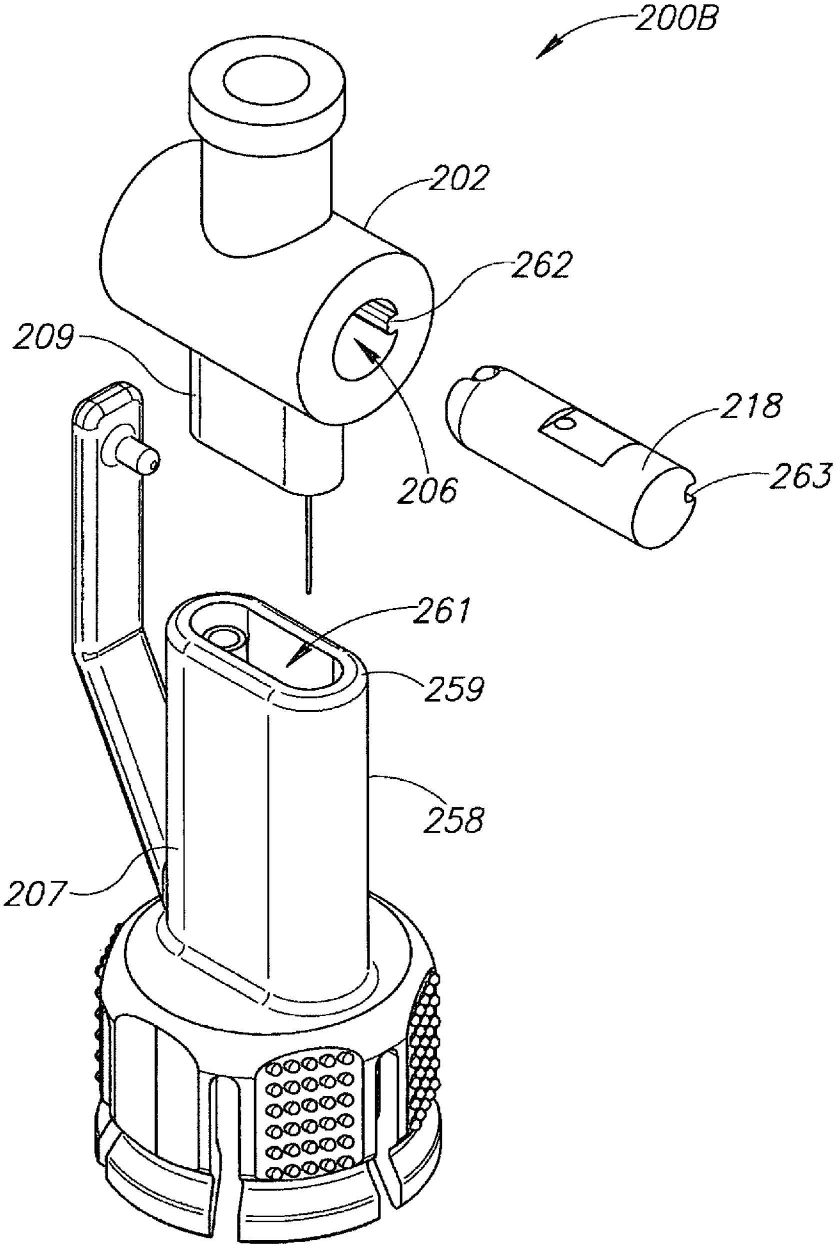
FIG. 17 is a pictorial representation of yet another embodiment of FIG. 8's device with a vial adapter having an elliptically shaped stem and stem tip with a stem tip cavity.

FIG. 17 show an inline liquid drug medical device 200B similar in construction and operation to the device 200 and therefore similar parts are likewise numbered. The device 200B differs from the device 200 insofar the former 200B includes an elliptically shaped stem 258 and stem tip 259 with a stem cavity 261, and a bore 206 which is cylindrically shaped and includes a keyed protrusion 262 extending therealong for fitting into a groove 263 in the flow control member 218. The keyed protrusion 262 and the groove 263 are configured for preventing rotation of the flow control member 218 inside the bore 206.

While the invention has been described with respect to a limited number of embodiments, it will be appreciated that many variations, modifications, and other applications of the invention can be made within the scope of the appended claims.

The invention claimed is:

1. An inline liquid drug medical device for use with a source of physiological solution and a medicinal vessel for reconstitution and administration of a liquid drug, the device having a longitudinal device axis, and comprising:

(a) a housing having a first port for fluid connection with the source of physiological solution, a second port for fluid connection with the medicinal vessel, a third port for liquid drug administration, and a bore transversely disposed with respect to the longitudinal device axis and in flow communication with said first port, said second port and said third port;

(b) a flow control member linearly displaceable and slidable along said bore from a first flow control position, establishing flow communication between said first port and said second port for liquid drug reconstitution purposes to a second flow control position, establishing flow communication between said first port and said third port for liquid drug administration purposes;

(c) an actuating mechanism that is manually operated, said actuating mechanism being rotatable about an axis of rotation co-directional with the longitudinal axis and having an initial liquid drug reconstitution position corresponding with said first flow control position and a subsequent liquid drug administration position corresponding to said second flow control position, said actuating mechanism having an internal cam surface bearing against said flow control member, and said internal cam surface having a first separation S1 relative to said axis of rotation in said liquid drug reconstitution position and a second separation S2 relative to said axis of rotation in said liquid drug administration position where said second separation S2 is smaller than said first separation S1, whereby manual actuation of said actuating mechanism from said liquid drug reconstitution position to said liquid drug administration position applies a radial actuation force for imparting a linear displacement force urging said flow control member to slide along said bore from said first flow control position to said second flow control position; and (d) a vial adapter for snap fitting onto the medicinal vessel and including a fluid conduit member with a proximal end in flow communication with said second port and a distal end in flow communication with a puncturing cannula extending into the medicinal vessel on the medicinal vessel's attachment to said vial adapter, and said vial adapter being removably attached to said housing along a line of detachment co-directional with the longitudinal device axis.

2. The device according to claim 1, wherein said vial adapter is rotationally detachable from said housing and said rotational detachment simultaneously actuates said actuating mechanism from said liquid drug reconstitution position to said liquid drug administration position.

3. The device according to claim 1, wherein said axis of rotation is co-axial with the longitudinal device axis.

4. The device according to claim 1, wherein said flow control member includes a peripheral cylindrical surface with a longitudinal flow cutout in flow communication with said first port in said first flow control position and said second flow control position, and a flow channel for establishing flow communication between said flow cutout and said second port in said first flow control position, and said flow cutout and said third port in said second flow control position.

5. The device according to claim 4, wherein said flow channel is a lumen extending through said flow control member.

6. The device according to claim 4, wherein said flow channel is a semi-circular flow channel on said peripheral cylindrical surface.

* * * * *